(12) United States Patent
Rai et al.

(10) Patent No.: US 11,488,017 B2
(45) Date of Patent: Nov. 1, 2022

(54) SYSTEM AND METHOD FOR MONITORING AND QUALITY EVALUATION OF PERISHABLE FOOD ITEMS

(71) Applicant: Tata Consultancy Services Limited, Mumbai (IN)

(72) Inventors: Beena Rai, Pune (IN); Jayita Dutta, Pune (IN); Parijat Deshpande, Pune (IN); Shankar Balajirao Kausley, Pune (IN); Shirish Subhash Karande, Pune (IN); Manasi Samarth Patwardhan, Pune (IN); Shashank Madhukar Deshmukh, Pune (IN)

(73) Assignee: Tata Consultancy Services Limited, Mumbai (IN)

(*) Notice: Subject to any disclaimer, the term of this patent is extended or adjusted under 35 U.S.C. 154(b) by 437 days.

(21) Appl. No.: 16/783,755

(22) Filed: Feb. 6, 2020

(65) Prior Publication Data
US 2020/0250531 A1    Aug. 6, 2020

(30) Foreign Application Priority Data
Feb. 6, 2019   (IN) .............................. 201921004783

(51) Int. Cl.
*G06N 3/08* (2006.01)
*G06N 3/04* (2006.01)

(52) U.S. Cl.
CPC ............. *G06N 3/08* (2013.01); *G06N 3/0445* (2013.01); *G06N 3/0454* (2013.01)

(58) Field of Classification Search
CPC .... G06K 9/6228; G06K 9/6261; G06N 20/10; G06N 20/20; G06N 3/0445;
(Continued)

(56) References Cited

U.S. PATENT DOCUMENTS

| 8,747,775 B2 | 6/2014 | Sandvick |
| 2018/0114415 A1 | 4/2018 | Mattingly et al. |

(Continued)

FOREIGN PATENT DOCUMENTS

| CN | 108224894 | 6/2018 |
| CN | 108872218 | 11/2018 |

OTHER PUBLICATIONS

Hajmeer et al, "Computational neural networks for predictive microbiology II. Application to microbial growth", 1997 (Year: 1997).*

(Continued)

*Primary Examiner* — Ruiping Li
(74) *Attorney, Agent, or Firm* — Finnegan, Henderson, Farabow, Garrett & Dunner, LLP

(57) ABSTRACT

This disclosure relates generally to a system and method for monitoring and quality evaluation of perishable food items in quantitative terms. Current technology provides limited capability for controlling environmental conditions surrounding the food items in real-time or any quantitative measurement for the degree of freshness of the perishable food items. The disclosed systems and methods facilitate in quantitative determination of freshness of food items by utilizing sensor data and visual data obtained by monitoring the food item. In an embodiment, the system utilizes a pre-trained CNN model and a RNN model, where the pertained CNN model is further fine-tined while training the RNN model to provide robust quality monitoring of the food items. In another embodiment, a rate kinetic based model is utilized for determining reaction rate order of the food item at a particular post-harvest stage of the food item so as to determine the remaining shelf life thereof.

11 Claims, 27 Drawing Sheets

(58) Field of Classification Search
CPC .... G06N 3/0454; G06N 3/084; G06V 10/454; G06V 10/751; G06V 10/82; G16Y 10/05; G16Y 20/20; G16Y 40/10
See application file for complete search history.

(56) References Cited

U.S. PATENT DOCUMENTS

2020/0253415 A1* 8/2020 Stork genannt Wersborg ............ A47J 36/32
2021/0311011 A1* 10/2021 Overcash ........... G06Q 30/0185

OTHER PUBLICATIONS

Annese, V.F. et al. "On-line Shelf-Life Prediction in Perishable Goods Chain Through the Integration of WSN Technology with a $1^{st}$ Order Kinetic Model," *2015 IEEE 15$^{th}$ International Conference on Environment and Electrical Engineering (EEEIC)*, Rome, Italy, Jun. 10-13, 2015; 7 pages.

* cited by examiner

TIME T= DAY 1 TO T=DAY 26
R2=0.84
R2 < 0.95

TIME T= DAY 1 TO T=DAY 26
R2=0.86 (R2 < 0.95)

TIME T= DAY 1 TO T=DAY 26
R2=0.87 (R2 < 0.95)

Zero order kinetic model for day t=0 to t=10 days

TIME T=1 to T=N-16
TIME T= DAY 1 TO T=DAY 10
R2=0.89   R2 < 0.95

First order kinetic model for day t=0 to t=10 days

TIME T=1 to T=N-16
TIME T= DAY 1 TO T=DAY 10
R2=0.89   R2 < 0.95

TIME T=1 to T=N-21
TIME T= DAY 1 TO T=DAY 5
R2=0.96
R2 >0.95
STAGE 2

STAGE 1 > TIME T= DAY 1 TO T=DAY 5
STAGE 2 > TIME T= DAY 5 TO T=DAY 21
R2=0.9546
R2 > 0.95

TABLE II

| Date | Day | Storage condition - I (Temperature 10 °C and relative humidity (RH) 90%) | | Storage condition - II (Temperature 25 °C and relative humidity (RH) 45%) | |
|---|---|---|---|---|---|
| | | Weight (g) | Weight loss (%) | Weight (g) | Weight loss (%) |
| 4-Sep-18 | 1st | 1042.3 | 0.00 | 1037.4 | 0 |
| 5-Sep-18 | 2nd | 1039.9 | 0.23 | 1033.3 | 0.40 |
| 6-Sep-18 | 3rd | 1039.4 | 0.28 | 1031.1 | 0.61 |
| 7-Sep-18 | 4th | 1037.7 | 0.44 | 1028.6 | 0.85 |
| 8-Sep-18 | 5th | 1037.4 | 0.47 | 1027.1 | 0.99 |
| 10-Sep-18 | 7th | 1035.7 | 0.63 | 1021.4 | 1.54 |
| 11-Sep-18 | 8th | 1035.1 | 0.69 | 1018.5 | 1.82 |
| 12-Sep-18 | 9th | 1034.5 | | 1016.5 | 2.01 |

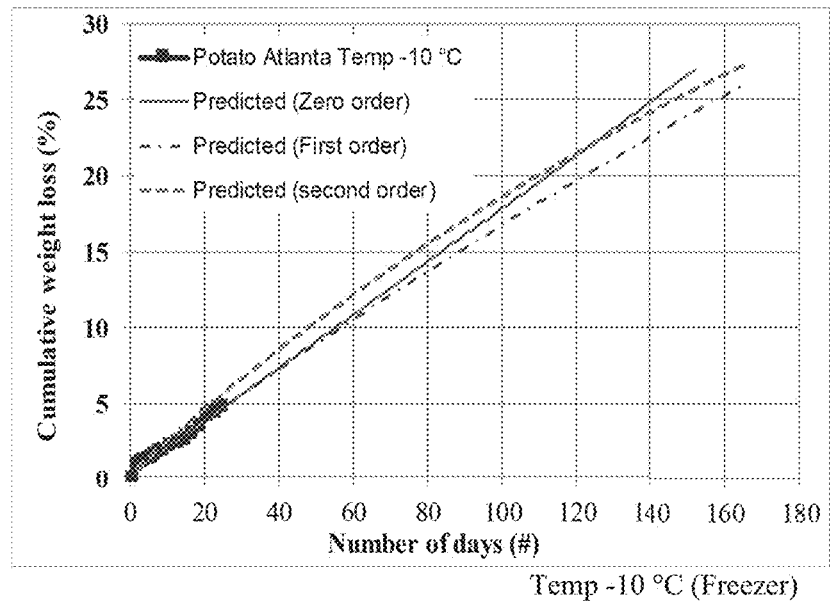
FIG. 11I  Temp -10 °C (Freezer)
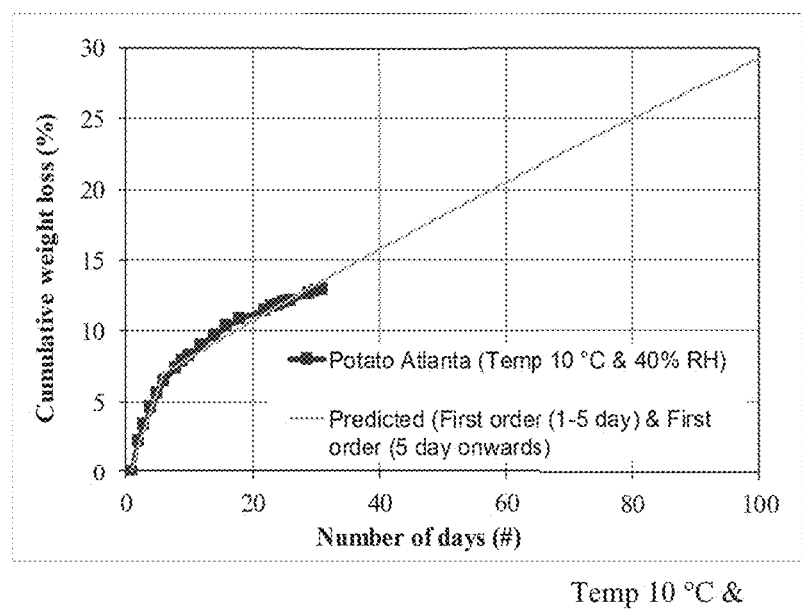
FIG. 11J  Temp 10 °C & 40% RH (Freeze)

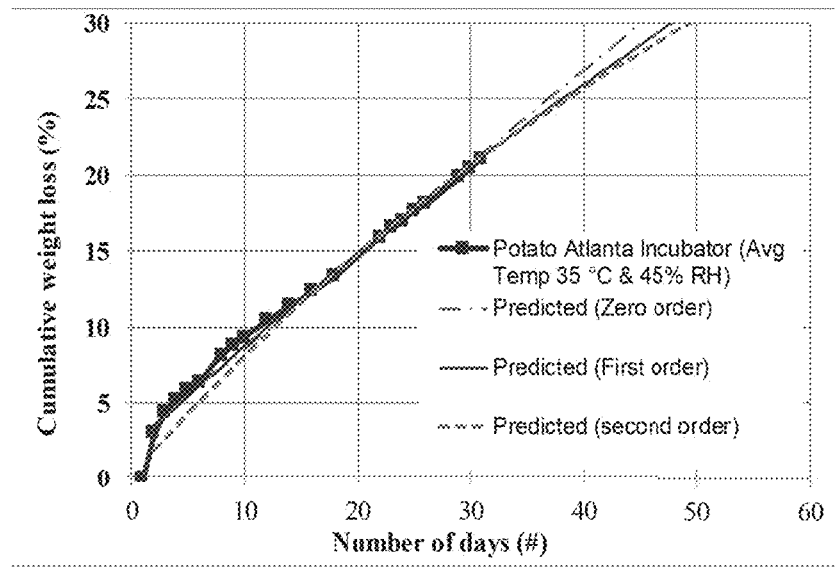
FIG. 11K  Temp 35 °C & 40% RH (Incubator)
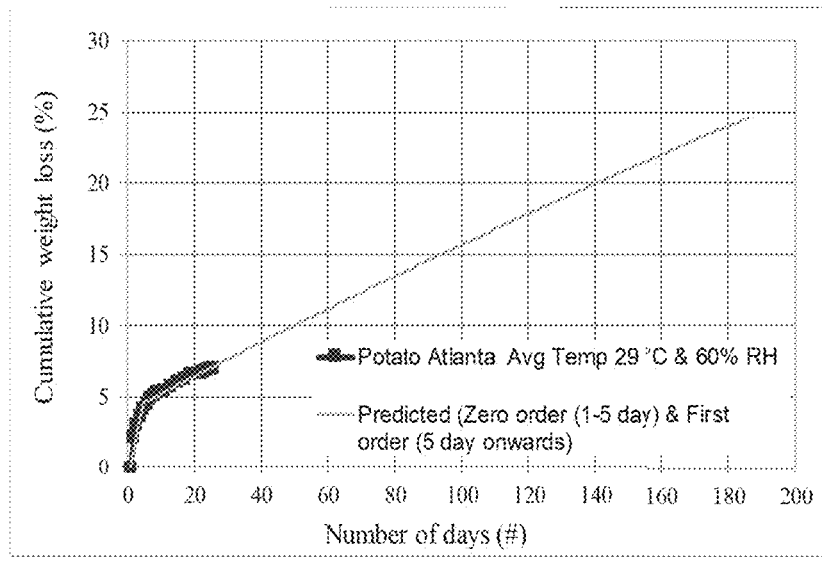
FIG. 11L  Temp 29 °C & 60% RH (Ambient)

Storage conditions
A -10 °C (Freezer)           B 10 °C & 40 % RH (Freeze)
C 29 °C & 60 % RH (Ambient)   D 35 °C & 40 % RH (Incubator)

Storage conditions
A -10 °C (Freezer)           B 10 °C & 40 % RH (Freeze)
C 29 °C & 60 % RH (Ambient)   D 35 °C & 40 % RH (Incubator)

| Temperature (°C) | Relative humidity(%) | Second order rate constant (k) |
|---|---|---|
| 25 | 50 | 0.0000020 |
| 25 | 60 | 0.0000010 |
| 25 | 70 | 0.0000010 |
| 25 | 90 | 0.0000006 |

| Storage condition | Weight loss (15%) | First sprout formation | Sprout formation (50%) | Fungal growth | Brown colour of chips |
|---|---|---|---|---|---|
| 25°C & RH 50% | 74 | 12 | 18 | >60 | >60 |
| 25°C & RH 60% | 147 | 9 | 19 | >60 | >60 |
| 25°C & RH 70% | 152 | 11 | 18 | >60 | >60 |
| 25°C & RH 90% | 257 | 11 | 22 | >60 | >60 |
| 18°C & RH 50% | 147 | 11 | 20 | >60 | >60 |
| 10°C & RH 40% | 74 | >90 | >90 | >60 | >60 |
| 5°C & RH 90% | 193 | >90 | >90 | >60 | >60 |
| 5°C | 257 | >90 | >90 | >60 | <50 |

FIG. 11S

SYSTEM AND METHOD FOR MONITORING AND QUALITY EVALUATION OF PERISHABLE FOOD ITEMS

PRIORITY CLAIM

This U.S. patent application claims priority under 35 U.S.C. § 119 to: India Application No. 201921004783, filed on Feb. 6, 2019. The entire contents of the aforementioned application are incorporated herein by reference.

TECHNICAL FIELD

The disclosure herein generally relates to monitoring and evaluation systems, and, more particularly, to system and method for monitoring and quality evaluation of perishable food items.

BACKGROUND

Amongst various food items used and consumed in various industries, perishable food items forms a huge percentage. Such food items, if not managed properly, for instance during transport and/or storage may pose major health hazards subjected to consumption of partially or fully spoiled food products such as dairy products, fish, meat raw vegetables post-harvest fruits, and so on. It is highly essential to monitor perishable food item/commodities over a period of time to ensure quality.

Sometimes consumption of certain perishable food items may be unhealthy due to change in certain composition of the food item, change in certain physical parameters like temperature, pressure, humidity, emission of some harmful gasses like methane, ethylene, ammonia etc. change in pH, increase of $CO_2$ content therein, change in moisture content therein, and so on. The degradation may not be visible via change in color or by mere visual observation.

SUMMARY

Embodiments of the present disclosure present technological improvements as solutions to one or more of the above-mentioned technical problems recognized by the inventors in conventional systems. For example, in one embodiment, a method for monitoring and quality evaluation of perishable food items is provided. The system includes obtaining input data comprising visual data and sensory data associated with a food item enclosed in a networked framework, via one or more hardware processors, wherein the visual data and sensory data are time-series data and comprises characteristics indicative of freshness of the food item at a plurality of lifecycle stages. Further the method includes obtaining, via the one or more hardware processors, a food freshness vector using the input data and one or more machine learning (ML) models. Obtaining the food freshness vector includes generating, by a pre-trained convolution neural network (CNN) model, a first vector embedding of the food item at a time-instance using the visual data, the pre-trained CNN model trained as a generic food item classifier using a plurality of images comprising the visual data of a plurality of food items for a plurality of time-instances associated with the plurality of lifecycle stages. Further, the method includes concatenating the first vector embedding and a second vector embedding to obtain a concatenated vector embedding at the time-instance. The second vector embedding is obtained from the sensory data of the input data. Also the method includes obtaining, by fine-tuning the pre-trained CNN model along with the training of a Recurrent Neural Network (RNN), a third vector embedding associated with the food item at the time instance using the concatenated vector embedding, wherein the third vector embedding indicative of a lifecycle stage of the food item at the time instance, wherein the RNN is trained using the time series data of the visual data and the sensory data of the food item aging over a period of time. Moreover, the method includes comparing, using vector similarity measure, the food freshness vector of the food item at the lifecycle stage from amongst the plurality of lifecycle stages with a digital signature of the food item, via the one or more hardware processors, wherein the food freshness vector of the food item obtained by feeding the visual input of the food item to the fine-tuned CNN model, and wherein the digital signature of the food item is a digitized vector representation of the food item, indicative of freshness of the food item at a target lifecycle stage.

In another aspect, a system for monitoring and quality evaluation of perishable food items is provided. The system includes one or more memories; and one or more first hardware processors, the one or more first memories coupled to the one or more first hardware processors, wherein the one or more first hardware processors are configured to execute programmed instructions stored in the one or more first memories, to obtain input data comprising visual data and sensory data associated with a food item enclosed in a networked framework, wherein the visual data and sensory data are time-series data and comprises characteristics indicative of freshness of the food item at a plurality of lifecycle stages. The one or more first hardware processors are configured to obtain a food freshness vector using the input data and one or more machine learning (ML) models. The one or more first hardware processors are configured to obtain the food freshness vector by generating, by a pre-trained convolution neural network (CNN) model, a first vector embedding of the food item at a time-instance using the visual data, the pre-trained CNN model trained as a generic food item classifier using a plurality of images comprising the visual data of a plurality of food items for a plurality of time-instances associated with the plurality of lifecycle stages. The one or more first hardware processors are further configured to concatenate the first vector embedding and a second vector embedding to obtain a concatenated vector embedding at the time-instance, wherein the second vector embedding obtained from the sensory data of the input data. Further, the one or more first hardware processors are configured to obtain, by fine-tuning the pre-trained CNN model along with the training of a Recurrent Neural Network (RNN), a third vector embedding associated with the food item at the time instance using the concatenated vector embedding, wherein the third vector embedding indicative of a lifecycle stage of the food item at the time instance, wherein the RNN is trained using the time series data of the visual data and the sensory data of the food item aging over a period of time. Furthermore, the one or more first hardware processors are configured to compare, using vector similarity measure, the food freshness vector of the food item at the lifecycle stage from amongst the plurality of lifecycle stages with a digital signature of the food item, wherein the food freshness vector of the food item obtained by feeding the visual input of the food item to the fine-tuned CNN model, and wherein the digital signature of the food item is a digitized vector representation of the food item, indicative of freshness of the food item at a target lifecycle stage.

In another aspect, a non-transitory computer readable medium for method for monitoring and quality evaluation of perishable food items is provided. The method includes obtaining input data comprising visual data and sensory data associated with a food item enclosed in a networked framework, via one or more hardware processors, wherein the visual data and sensory data are time-series data and comprises characteristics indicative of freshness of the food item at a plurality of lifecycle stages. Further the method includes obtaining, via the one or more hardware processors, a food freshness vector using the input data and one or more machine learning (ML) models. Obtaining the food freshness vector includes generating, by a pre-trained convolution neural network (CNN) model, a first vector embedding of the food item at a time-instance using the visual data, the pre-trained CNN model trained as a generic food item classifier using a plurality of images comprising the visual data of a plurality of food items for a plurality of time-instances associated with the plurality of lifecycle stages. Further, the method includes concatenating the first vector embedding and a second vector embedding to obtain a concatenated vector embedding at the time-instance. The second vector embedding is obtained from the sensory data of the input data. Also the method includes obtaining, by fine-tuning the pre-trained CNN model along with the training of a Recurrent Neural Network (RNN), a third vector embedding associated with the food item at the time instance using the concatenated vector embedding, wherein the third vector embedding indicative of a lifecycle stage of the food item at the time instance, wherein the RNN is trained using the time series data of the visual data and the sensory data of the food item aging over a period of time. Moreover, the method includes comparing, using vector similarity measure, a food freshness vector of the food item at the lifecycle stage from amongst the plurality of lifecycle stages with a digital signature of the food item, via the one or more hardware processors, wherein the food freshness vector of the food item obtained by feeding the visual input of the food item to the fine-tuned CNN model, and wherein the digital signature of the food item is a digitized vector representation of the food item, indicative of freshness of the food item at a target lifecycle stage.

In yet another embodiment, a processor-implemented is method. The method includes obtaining a rate kinetic data associated with a food item enclosed in a networked framework, via one or more hardware processors. wherein the rate kinetic data comprises a time-series data having a plurality of attributes indicative of freshness of the food item. Further the method includes selectively partitioning the rate kinetic data into a plurality of post-harvest lifecycle stages of the food item based on a reaction rate order associated with one or more time intervals of each of the plurality of post-harvest lifecycle stages, via the one or more hardware processors, wherein the reaction rate order associated with the one or more time intervals of each of the plurality of post-harvest lifecycle stages is determined by a trained rate kinetic model. Furthermore, the method includes estimating, based at least on the reaction rate order associated with the one or more time intervals and the plurality of attributes, a plurality of values of shelf-life of the food item during each of the one or more time intervals, via the one or more hardware processors. Also, the method includes aggregating, via the one or more hardware processors, a set of values of the shelf-life from amongst the plurality of values of the shelf-life corresponding to each attribute of the plurality of attributes. Also, the method includes selecting, from amongst the set of values of the shelf-life, a minimum value of shelf-life as the food freshness value of the food item.

In still another embodiment, a system for monitoring and quality evaluation of perishable food items is provided. The system includes one or more memories; and one or more first hardware processors, the one or more first memories coupled to the one or more first hardware processors, wherein the one or more first hardware processors are configured to execute programmed instructions stored in the one or more first memories, to obtain a rate kinetic data associated with a food item enclosed in a networked framework, wherein the rate kinetic data comprises a time-series data having a plurality of attributes indicative of freshness of the food item. Further, the one or more hardware processors are further configured by the instructions to selectively partition the rate kinetic data into a plurality of post-harvest lifecycle stages of the food item based on a reaction rate order associated with one or more time intervals of each of the plurality of post-harvest lifecycle stages, wherein the reaction rate order associated with the one or more time intervals of each of the plurality of post-harvest lifecycle stages is determined by a trained rate kinetic model. Furthermore, the one or more hardware processors are further configured by the instructions to estimate, based at least on the reaction rate order associated with the one or more time intervals and the plurality of attributes, a plurality of values of shelf-life of the food item during each of the one or more time intervals. Also the one or more hardware processors are further configured by the instructions to aggregate a set of values of the shelf-life from amongst the plurality of values of the shelf-life corresponding to each attribute of the plurality of attributes. Also, the one or more hardware processors are further configured by the instructions select, from amongst the set of values of the shelf-life, a minimum value of shelf-life as the food freshness value of the food item.

In still another aspect, a non-transitory computer readable medium for method for monitoring and quality evaluation of perishable food items is provided. The method includes obtaining a rate kinetic data associated with a food item enclosed in a networked framework, wherein the rate kinetic data comprises a time-series data having a plurality of attributes indicative of freshness of the food item. Further the method includes selectively partition the rate kinetic data into a plurality of post-harvest lifecycle stages of the food item based on a reaction rate order associated with the one or more time intervals of each of the plurality of post-harvest lifecycle stages, wherein the reaction rate order associated with the one or more time intervals of each of the plurality of post-harvest lifecycle stages is determined by a trained rate kinetic model. Furthermore, the method includes estimating, based at least on the reaction rate order associated with the one or more time intervals and the plurality of attributes, a plurality of values of shelf-life of the food item during each of the one or more time intervals. Also, the method includes aggregating a set of values of the shelf-life from amongst the plurality of values of the shelf-life corresponding to each attribute of the plurality of attributes. Also, the method includes selecting, from amongst the set of values of the shelf-life, a minimum value of shelf-life as the food freshness value of the food item It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

FIGS. 11I-11L illustrates rate kinetic models for potatoes stored at different environmental conditions, according to an example embodiment of the present disclosure.

FIG. 11S illustrates an example of shelf-life attribute for various storage conditions, in accordance with an example scenario.

DETAILED DESCRIPTION

Figure 1:
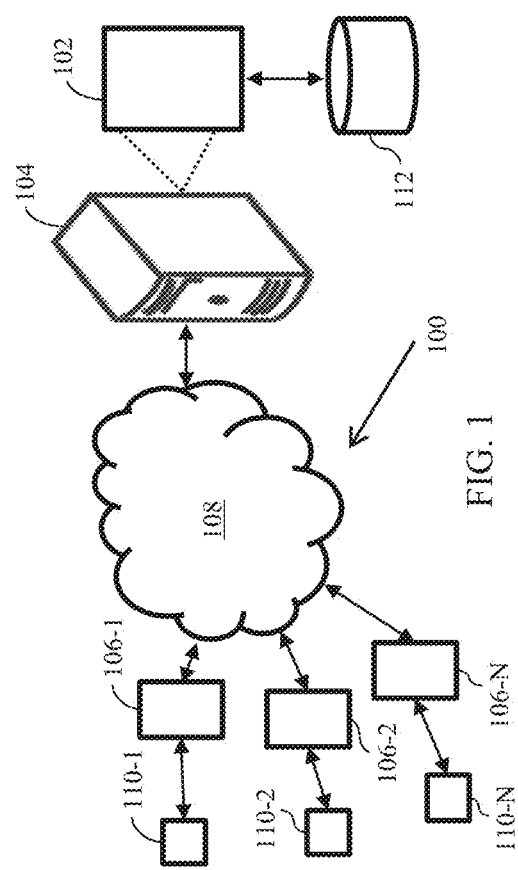
FIG. 1 illustrates a network environment implementing a system for monitoring and quality evaluation of perishable food items, according to an embodiment of the present subject matter.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Various conventional techniques are available for monitoring and quality evaluation of perishable food items. The conventional technologies available for said monitoring and quality evaluation involves sensing/monitoring based on a single parameter like food item surrounding temperature, odor or visual observation or pictorial changes or gasses emitted or by chemical changes observed over time. Current technology, however, does not allow simultaneous sensing of orthogonal parameters over time. Herein, orthogonal parameters refer to statistically independent parameters. Sensing of orthogonal parameters implies that the sensed parameters that are used for prediction of degree of food freshness are independent of one another and mutually exclusive.

Typically, such sensing is done either at source or during transit/storage but there exist no provision for continuous food monitoring at source, during storage and in transit. Such conventional technology is limited in a display capability to indicate food freshness parameters to all the stakeholders in the food supply chain. Moreover, available systems have limited or no capability for controlling the environmental conditions surrounding the food items in real-time. Typical monitoring of perishable food items merely provides qualitative analysis but does not provide any quantitative measurement for the degree of freshness of the perishable food items. Current techniques do not have provisions for online monitoring and prediction of remaining shelf life at a prior date and hence no provision exists for repurposing the perishable item much before it starts degrading and hence reduce wastage. Accordingly, an automated system for monitoring and quality evaluation of perishable food items is important so as to monitor various mutually exclusive parameters periodically, and ascertain health safety.

Various embodiments of the present disclosure provide system and method for monitoring and quality evaluation of perishable food items. Particularly, the disclosed system is capable of predicting freshness of perishable food items at source, during transit and storage by utilizing a continuous controlled monitoring technique. In an embodiment, the system includes a customized model specific to a given perishable food items. The system is capable of predicting food quality /freshness against a standard of the given perishable food item based on the data model, the composition of the food item and stoichiometric equations that governs the stages of the food item post-harvest till the food item is consumed or used for processing during the lifecycle thereof. Since the system is capable of predicting the food quality in quantitative terms, it enables repurposing food and reducing food loss and food wastage based on remaining shelf life.

In an embodiment, the disclosed system includes a multi-parameter intelligent model of the selected perishable food item to be monitored. The system combines explicitly collected sensor data along with implicit visual characteristics associated with the perishable foods to determine food freshness or perishable food item shelf life over time. In an embodiment, the model receives multiple sensory data as well as visual data input from an integrated framework, and then determines freshness of the perishable food items as a function of multiple varying parameters. In an embodiment, the system generates a digital signature for an ideal stage of the perishable food item as a standardization technique to determine freshness of the perishable food item. The digital signature of the food item is a digitized vector representation of the food item, indicative of freshness of the food item at a target lifecycle stage. In an embodiment, the target lifecycle stage may be a lifecycle stage of the food item. A detailed description of the above described system for monitoring of perishable food items is shown with respect to illustrations represented with reference to FIGS. 1 through 7C.

In another embodiment, a method and system are provided for monitoring and quality evaluation of perishable food items based on a rate kinetic model. The rate kinetic model includes rate kinetic of zero order, first order and second order. The disclosed system is capable of monitoring the rate kinetics (or rate of change of attribute data) of the food item at any given time interval and based on the same determines the reaction rate order in said interval. The system further determines a shelf-life of the food item under consideration based on the reaction rate order and attributes to predict the shelf-life of the food item. A detailed description of the above described system for monitoring of perishable food items is shown with respect to illustrations represented with reference to FIGS. 1-4 and FIGS. 8-11S.

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Referring now to the drawings, and more particularly to FIG. 1 through 11S, where similar reference characters denote corresponding features consistently throughout the figures, there are shown preferred embodiments and these embodiments are described in the context of the following exemplary system and/or method.

FIG. 1 illustrates a network environment 100 implementing a system 102 for monitoring perishable food items, according to an embodiment of the present subject matter. The system 102 is capable of estimating freshness quality of the perishable food items/shelf life as a function of multiple mutually exclusive sensed parameters associated with the perishable food items, and hence enables not only the qualitative analysis but also quantitative estimate of the freshness of the perishable food item. Hereinafter, for the brevity of description, the 'perishable food items/commodities' may be referred to as 'food item'.

In an embodiment, the system 102 may receive sensory data and visual data based on the monitoring of the food item from a networked framework, for example networked framework. Herein, it will be understood that said networked framework is capable of incorporating multiple mutually exclusive sensors, including but not limited to, pH sensor, optical sensor, gas sensor (for instance, $O_2$, $CO_2$, $NH_3$, methane, ethylene, and so on), temperature sensor, humidity sensor, color sensor, NIR sensor with micro spectrophotometer, ultrasonic sensor, GSR sensor, and so on integrated inside a customized enclosure capable of periodic, synchronized data logging corresponding to the food item. Herein, the ultrasonic sensor measures any new growth by using ultrasonic waves, NIR sensor with micro spectrophotometer obtains spectra of sub-micron levels, the GSR sensor suitably modified as per requirements measures minute, delicate changes with respect to skin resistance of the perishable item which perhaps mark the beginning of degradation and cannot be measures otherwise.

In an embodiment, the mutually exclusive sensors may be integrated in a smart plate. The aforementioned networked framework enables multivariate sensing and monitoring of perishable food items like fish, meat, dairy products, post-harvest fruits and other perishable food items. In an embodiment, the sensors may include a modular configuration, and hence may be replaced based upon the food item. The food items may also be illuminated by various frequencies of light. In an embodiment, the disclosed framework may be a modular framework where any existing sensor can be removed or any new sensor can be plugged in as per requirements. Also, multiple sensors and multiple cameras may be installed inside a custom enclosure embodying the networked framework with parameter variation control such as, but not limited to, temperature, humidity, and so on to capture periodic changes in the food item from all directions depending upon the requirements. Herein, it will be understood that the disclosed networked framework is capable of automatically activating only those sensors from amongst a plurality of aforementioned sensors to which the food item responds. Depending on the choice of the food item, one or more sensors can be invoked and that model can be used for prediction of freshness of the food. For example, cheese may require pH sensor while fruits may require Ethylene and $CO_2$ sensors for monitoring. The networked framework for monitoring the food items and capturing the sensory data and the visual data therefrom is further described in the Indian Patent application no. 201821040783 titled, "Integrated Framework for Multimodal Sensing and Monitoring of Perishable Items" and is incorporated herein by reference.

The system 102 includes an intelligent model that may be pre-trained using multi-variate, multi-parameter, multi-modal sensory as well as visual data associated with food items. In real-time, the system 102 receives the sensory data and the visual data from the integrated networked framework monitoring the food item, and estimates a degree of freshness/quality therefrom by utilizing the intelligent model and digital signature of the selected food item. Herein, it will be understood that the term 'digital signature' refers to a representation of an ideal or near ideal food item.

The networked framework allows generating a digital signature of a perishable food item at a stage, where it is ideal for use as far as freshness in concerned. Such a digital signature can be used as a standard for evaluation of freshness of other food items to validate if their freshness is apt of its use.

Although the present disclosure is explained considering that the system 102 is implemented on a server, it may be understood that the system 102 may also be implemented in a variety of computing systems, such as a laptop computer, a desktop computer, a notebook, a workstation, a cloud-based computing environment and the like. It will be understood that the system 102 may be accessed by multiple users through one or more devices 106-1, 106-2 . . . 106-N, collectively referred to as devices 106 hereinafter, or applications residing on the devices 106. Examples of the devices 106 may include, but are not limited to, a portable computer, a personal digital assistant, a handheld device, a smartphone, a tablet Computer, a workstation and the like. The devices 106 are communicatively coupled to the system 102 through a network 108.

In an embodiment, the network 108 may be a wireless or a wired network, or a combination thereof. In an example, the network 108 can be implemented as a computer network, as one of the different types of networks, such as virtual private network (VPN), intranet, local area network (LAN), wide area network (WAN), the internet, and such. The network 106 may either be a dedicated network or a shared network, which represents an association of the different types of networks that use a variety of protocols, for example, Hypertext Transfer Protocol (HTTP), Transmission Control Protocol/Internet Protocol (TCP/IP), and Wireless Application Protocol (WAP), to communicate with each other. Further, the network 208 may include a variety of network devices, including routers, bridges, servers, computing devices, storage devices. The network devices within the network 108 may interact with the system 102 through communication links.

As discussed above, the system 102 may be implemented in a computing device 104, such as a hand-held device, a laptop or other portable computer, a tablet computer, a mobile phone, a PDA, a smartphone, and a desktop computer. The system 102 may also be implemented in a workstation, a mainframe computer, a server, and a network server. In an embodiment, the system 102 may be coupled to a data repository, for example, a repository 112. The repository 112 may store data processed, received, and generated by the system 102. In an alternate embodiment, the system 102 may include the data repository 112.

In an embodiment, the network environment 100 may be an IoT based environment comprising various hardware and software elements collectively configured to perform real-time data analytics in the smart computing environment, according to an exemplary embodiment of the disclosure. The IoT based platform backend may include a cloud server, for example the server 104 connected to a database, for example, the database 112. The system 100 further includes various IoT based devices, for example the devices 106 implemented on different smart devices such as smart phone, a telematics device, and so on enabling real-time analytics of sensor data. The system further includes various heterogeneous sensor devices, for example sensor devices 110-1, 110-2, 110-N (hereinafter collectively referred to as sensor devices 110) and so on, placed in the vicinity of smart computing environment connected with various IoT based devices 106. Alternatively, said sensor devices 110 may be embodied in the IoT based devices 106. Thus, the sensor devices 110 along with the IoT based devices 106 may collectively form an intelligent smart environment according to this exemplary embodiment.

Further, as illustrated in FIG. 1, the network environment 100 supports various connectivity options such as BLUETOOTH®, USB, ZigBee and other cellular services. In an exemplary embodiment, the system 102 interfaces with sensors 110 such as GPS, accelerometers, magnetic compass, audio sensors, camera sensors, and so on. Based on the data collected from various sensors, the system 102 with the help of various hardware and software platforms, collectively performs the task of scalable data analytics on the captured sensor data in any smart computing environment. The network environment enables connection of devices 106 such as Smartphone with the server 104, and accordingly with the database 112 using any communication link including Internet, WAN, MAN, and so on. In an exemplary embodiment, the system 102 is implemented to operate as a stand-alone device. In another embodiment, the system 102 may be implemented to work as a loosely coupled device to the smart computing environment. In an embodiment, the networked framework may be embodied in an enclosure in form of a closed chamber. An example of the chamber embodying the networked framework is described further with reference to FIG. 2.

Figure 2:
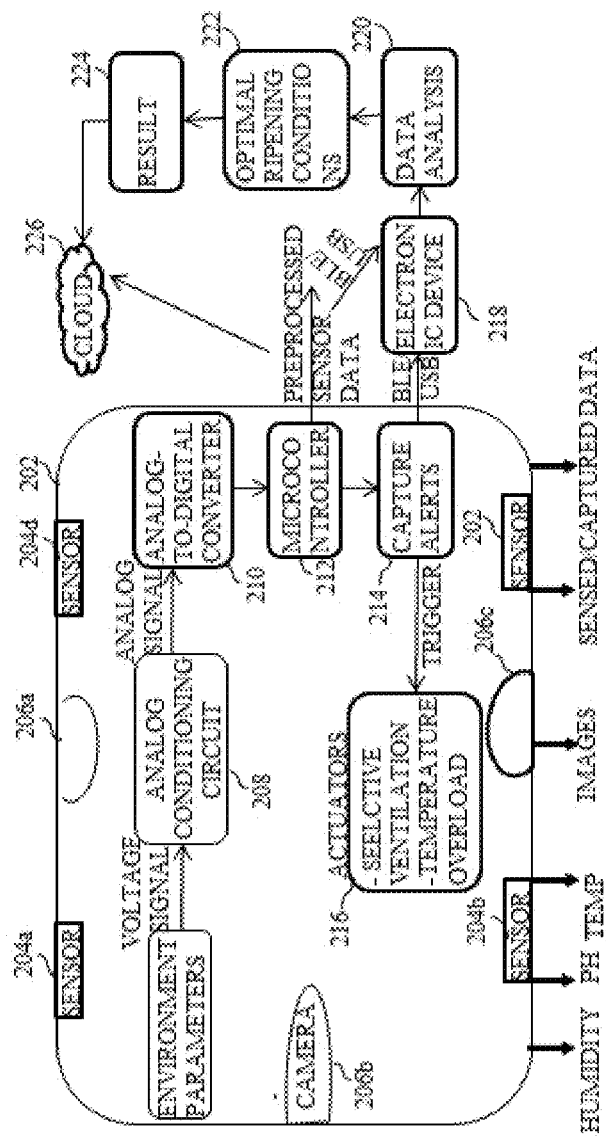
FIG. 2 is a process flow for monitoring and quality evaluation of perishable food items is disclosed, in accordance with an example embodiment

Referring now to FIG. 2, a process flow for monitoring of perishable food items is disclosed, in accordance with an example embodiment. As disclosed previously, the networked framework can be implemented for real time analysis of degree of freshness/quality at source, during storage and at transit. Furthermore, the networked framework may be able to predict the shelf life over the given conditions so that a feedback system can be developed to either alter the environmental conditions or take appropriate actions such as repurposing, transporting to a nearby location, and so on. Such quantitative analysis opens up avenues for repurposing the perishable item and thereby reducing wastage.

In an embodiment, the framework may be embodied in an enclosure, for instance an enclosure 202. The enclosure 202 may include multiple smart plates installed therein where environmental conditions at source or during storage or at transit can be recreated. For example as illustrated the enclosure includes sensor suites (each suite having multiple sensors) such as sensor suites 204a, 204b, 204c, and 204d (hereinafter referred to as sensor suites 204), and multiple media capturing devices/sensors such as devices 206a, 206b, 206c, 206d (hereinafter referred to as devices 206). The sensors of the sensor suites 204 along with the devices 206 captures sensory data and visual data, respectively pertaining to the food item. Said extensive synchronized data collection is followed by data filtration and data preprocessing periodically.

Said data can be interfaced with PC (for example a computer 208) and/or Bluetooth device (for example, a Bluetooth device 210) and/or Cloud (for example, cloud 212) to form IoT platform, for example an IoT platform 214. Such interfacing may be utilized for data analysis at 216.

Said data analysis facilitate in finding data correlations (or data analysis) at 218, via machine learning (ML) and/or artificial intelligence (AI) algorithms to develop models, thereby leading to a customized digital twin for quantitative prediction of quality, degree of freshness, remaining shelf life of the perishable food item at 220. Herein, the digital twin refers to a ML/AI based model that can quantitatively predict the quality of the perishable food item. Herein, the framework may be IoT enabled, thereby enabling storage of result 224 of the data analysis on a cloud 226 via for instance, Wi-Fi module and permits remote data access via for instance, internet. In an embodiment, the disclosed system for monitoring and quality estimation/prediction of perishable food items is described further with reference to FIG. 3.

Figure 3:
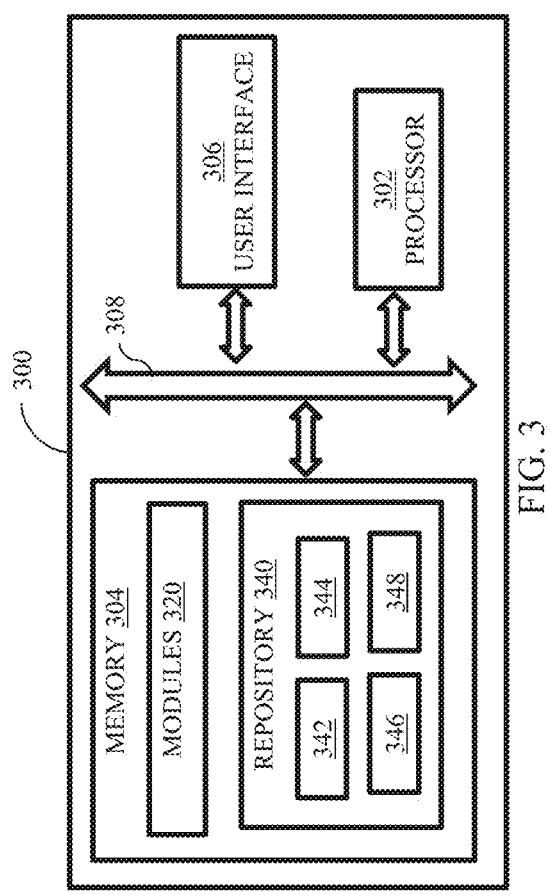
FIG. 3 is a functional block diagram of a system for monitoring and quality evaluation of perishable food items, in accordance with an example embodiment.

FIG. 3 illustrates a block diagram of a system 300, for example the system 102 (FIG. 1) for monitoring and quality estimation of the perishable food items, according to some embodiments of the present disclosure.

The system 300 includes or is otherwise in communication with one or more hardware processors such as a processor 302, at least one memory such as a memory 304, and an I/O interface 306. The processor 302, memory 304, and the I/O interface 306 may be coupled by a system bus such as a system bus 308 or a similar mechanism. The I/O interface 306 may include a variety of software and hardware interfaces, for example, a web interface, a graphical user interface, and the like. The interfaces 306 may include a variety of software and hardware interfaces, for example, interfaces for peripheral device(s), such as a keyboard, a mouse, an external memory, and a printer. Further, the interfaces 306 may enable the system 300 to communicate with other devices, such as web servers and external databases. The interfaces 306 can facilitate multiple communications within a wide variety of networks and protocol types, including wired networks, for example, local area network (LAN), cable, and so on, and wireless networks, such as Wireless LAN (WLAN), cellular, or satellite. For the purpose, the interfaces 306 may include one or more ports for connecting a number of computing systems with one another or to another server computer. The I/O interface 306 may include one or more ports for connecting a number of devices to one another or to another server.

The hardware processor 302 may be implemented as one or more microprocessors, microcomputers, microcontrollers, digital signal processors, central processing units, state machines, logic circuitries, and/or any devices that manipulate signals based on operational instructions. Among other capabilities, the hardware processor 302 is configured to fetch and execute computer-readable instructions stored in the memory 304.

The memory 304 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. In an embodiment, the memory 304 includes a plurality of modules 320 and a repository 340 for storing data processed, received, and generated by one or more of the modules 320. The modules 320 may include routines, programs, objects, components, data structures, and so on, which perform particular tasks or implement particular abstract data types. The repository 340, amongst other things, includes a system database 342 and other data 344. The other data 344 may include data generated as a result of the execution of one or more modules in the modules 320. The repository 340 may further include a sensory data 346 and image data 348 obtained during the monitoring of the food items, as will be explained further in detail below.

The system 300 is configured to perform monitoring and quality prediction of the perishable food items periodically. In an embodiment, the system 300 may receive sensory data 346 and image data 348 from the framework (for example, the framework explained with reference to FIG. 2).

The system 300 preprocesses the sensory data 346 and the image data 348. In an embodiment, the one or more hardware processors may facilitate preprocessing of the sensory data 346 and the image data 348, as is explained further in description below.

Figure 4:
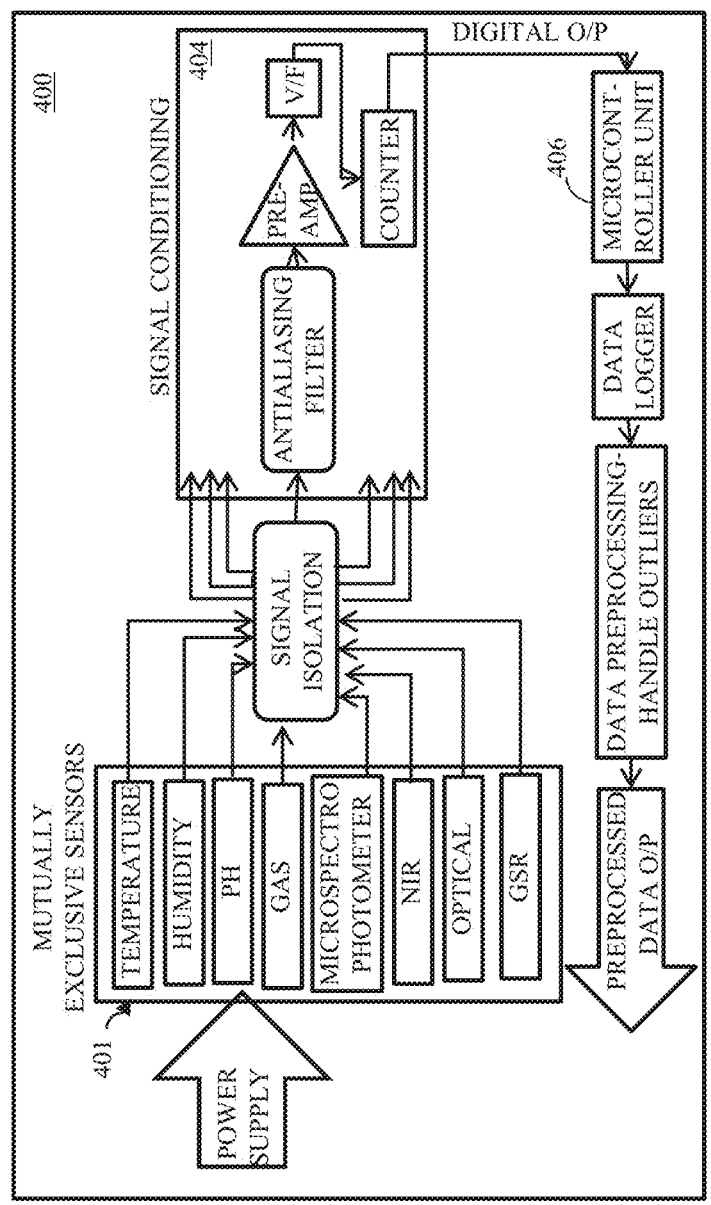
FIG. 4 is an example representation of signal processing components and circuitry of a system for monitoring and quality evaluation of perishable food items, according to some embodiments of the present disclosure.

Referring now to FIG. 4, an example representation of signal processing components and circuitry 400 (hereinafter referred to as circuitry 400) of a system, for example the system 300 is illustrated according to some embodiments of the present disclosure. Herein, the signal processing components and circuitry 400 is considered to be a part of the system 300. In other words, in the present embodiment, the system 300 is capable of preprocessing the sensory data and the visual/image data received from the framework by using the circuitry 400. However, it will be understood that in alternate embodiments, the circuitry may not be embodied in the system 300, instead the circuitry 400 may be embodied in the framework for preprocessing the visual/image data, and the system 300 may receive said preprocessed data from the framework.

As illustrated, sensed raw signal from the sensors framework 401 may be fed to a signal isolation circuit 402 to remove induced noise from the sensor signal(s), prevent ground looping in the communication network and provide proper isolation between the sensor signals. A signal conditioning and data pre-processing module 404 performs signal conditioning, which involves filtering of unwanted frequencies, followed by voltage amplification by the pre-amplifier for further digitization by a data acquisition equipment and finally for generating analog to digital output data streams to be further processed by the hardware processor(s) 406. Herein, the hardware processor 406 is similar to the hardware processor 302 (FIG. 3).

The quantified data can be used as an input for further applications which require quantifiable data. For example, for the perishable food item being monitored, the corresponding quantified data can be used to predict degree of food quality over time, which may be useful for repurposing of the food item and thereby reducing wastage of the food.

In an embodiment, the system 400 is used to qualify and quantify the degree of food freshness. For instance, the environmental conditions during food transit and food storage may be recreated in a controlled chamber and the collected data over time is used to predict the degree of freshness on the nth day. Moreover, based on the nth day data, the system can also predict the remaining shelf-life of the food product or predict the degree of freshness to appear on the n+5th day. Accordingly, the food can be repurposed based on the remaining shelf life and food wastage can be reduced. In an embodiment, the system analyses the collected mutually exclusive synchronized data to develop a digital twin (or an intelligent model) with capability of predicting food freshness over time, as described further with reference to FIG. 5.

Figure 5:
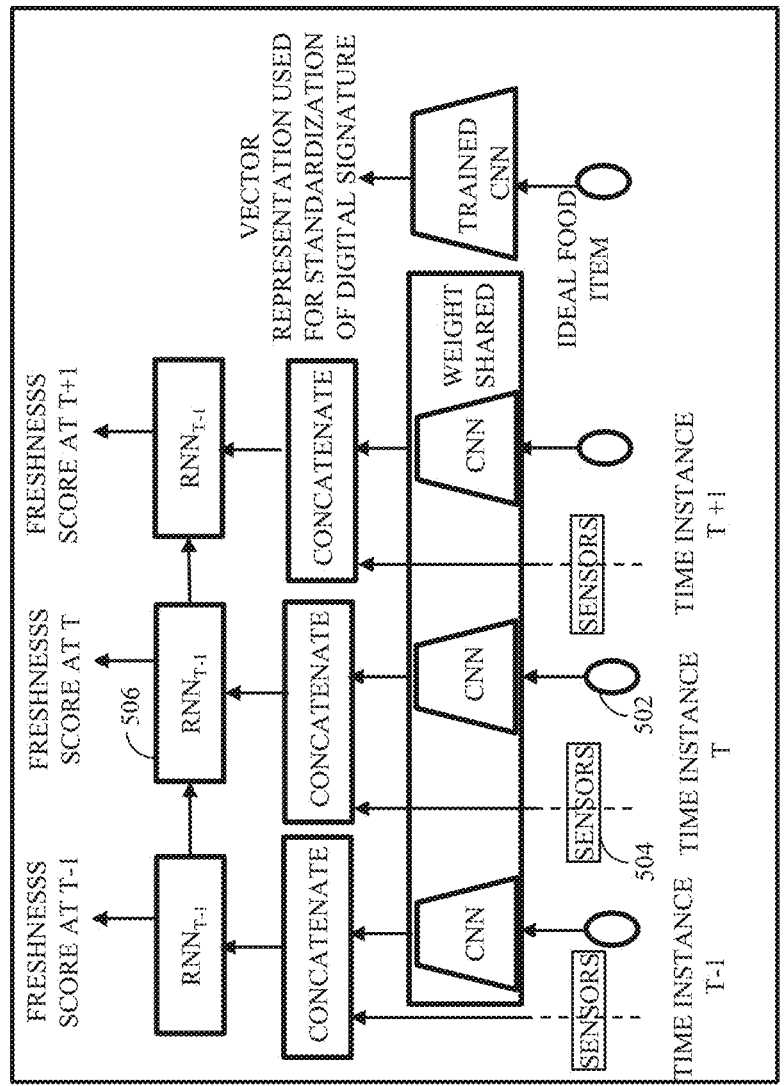
FIG. 5 illustrates an example of fine tuning a CNN model associated with a system for monitoring and quality evaluation of perishable food items, according to some embodiments of the present disclosure.
Figure 6:
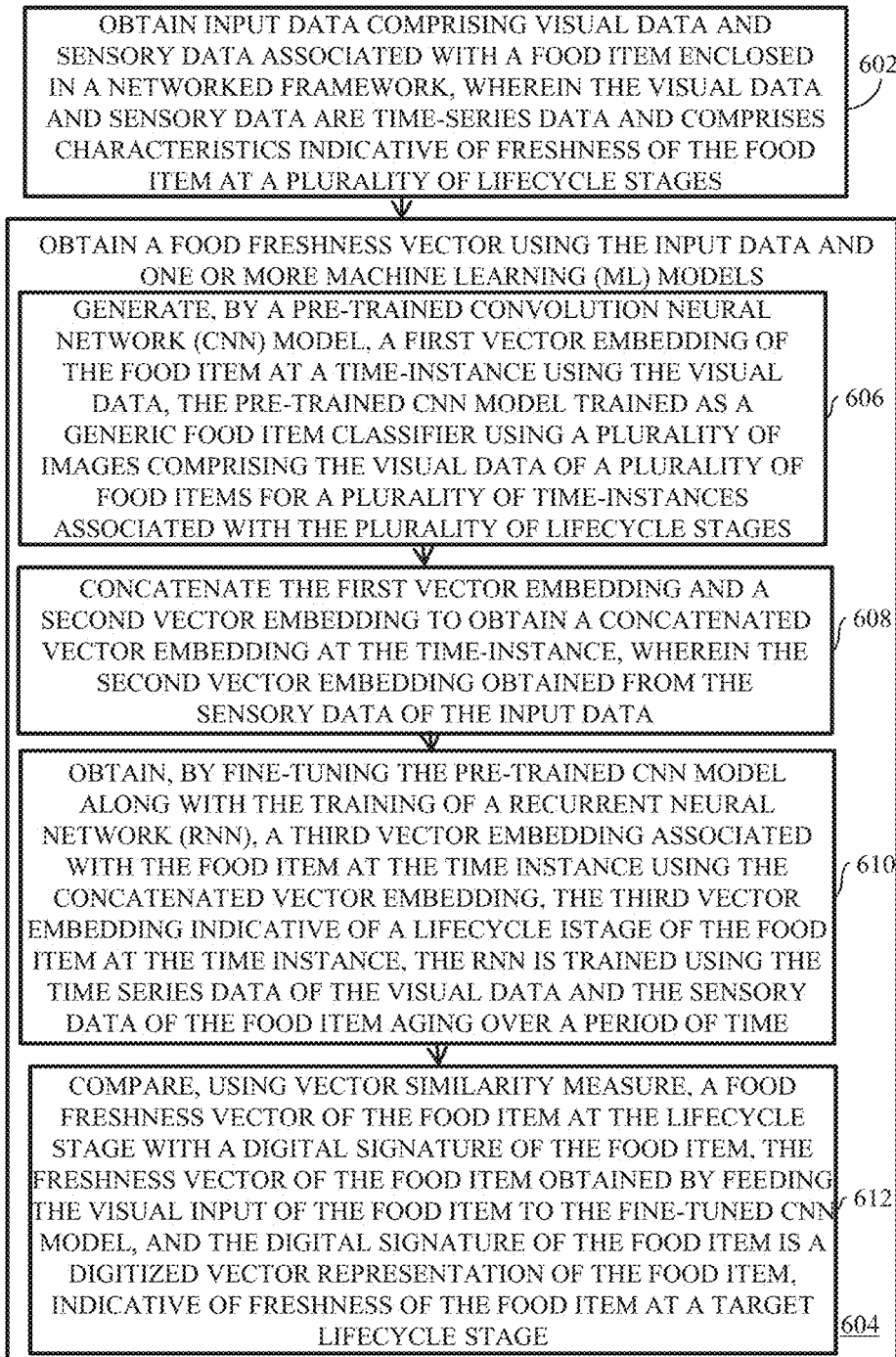
FIG. 6 illustrates an example flow diagram depicting a method for monitoring and quality evaluation of perishable food items, in accordance with an example embodiment.

Referring to FIG. 5 and FIG. 6 collectively, the monitoring and quality estimation of the perishable food items is described in further detail. For example, FIG. 5 illustrates an architecture diagram for a system 500 for monitoring and quality estimation of the perishable food items, in accordance with some embodiments of the present disclosure. FIG. 6 illustrates a flow diagram of a method for monitoring and quality estimation of the perishable food items, in accordance with an example embodiment.

The system 500 may be an example of the system 102 (FIG. 1) or the system 300 (FIG. 3). The system 500 includes a machine learning model that may be developed as per the nature of the perishable food item considering various parameters so as to serve as a basis for machine intelligence to achieve prediction with the capability to learn. In an embodiment, the machine learning model takes an input data including the sensory data as well as an image data captured by a high resolution camera feed as an input at 602 (FIG. 6). The input data is taken at a plurality of lifecycle stages of the food items. In an embodiment, the plurality of lifecycle stages may include the stages of the food item post-harvest till the food item is consumed or used for processing. For instance, for a food item such as banana, the plurality of lifecycle stages may include post-harvest stages of the banana, till the banana is consumed. Additionally or alternatively, the plurality of lifecycle stages of the banana may include stages till the banana is utilized for processing, for instance for making banana chips. In another example scenario, the plurality of lifecycle stages may include stages post processing, for instance, till the time the banana chips can be consumed.

The system 500 treats said input data as a time series data, where every time-instance takes the sensory data 502 and visual input 504, captured at a time instance in the life-time of a perishable food item, as an input. The output of the ML model predicts a degree and/or index of freshness of the food item in terms of a food freshness vector at every time instance (at 604 of FIG. 6), which may degrade as the time progresses. The food freshness vector of the food item can be obtained by feeding the visual input of the food item to a fine-tuned CNN model. The model can be a Recurrent Neural Network (RNN), for example RNN model 506 which takes into consideration the dependencies of prior time instances (t−1, t−2, . . . , 1) while predicting the output at time-instance t of the time series data. Taking the previous time-instances into consideration ensures that the freshness value of the food item at time instance t is not only a function of the sensory data and visual data at time t, but also takes the prior states into account while making the prediction, thereby enabling the system 500 to take into consideration the rate of change of sensory values as well as visual characteristics such as color, texture, and so on, while predicting the freshness of the food item at a time instance t.

The mathematical equations for specialized type of RNN networks called Long Short-Term Memory Networks (LSTMs) are as follows:

$$f_t = \sigma_g(W_f x_t + U_f c_{t-1} + b_f)$$

$$i_t = \sigma_g(W_i x_t + U_i c_{t-1} + b_i)$$

$$o_t = \sigma_g(W_o x_t + U_o c_{t-1} + b_o)$$

$$c_t = f_t \odot c_{t-1} + i_t \odot \sigma_c(W_c x_t + U_c c_{t-1} + b_c)$$

$$h_t = o_t \odot \sigma_h(c_t)$$

where $x_t$ is the input to the model at time instance t.
$c_t$ is the cell state of the model, which captures the history and
$h_t$ is the output of the hidden state at time instance t.

Herein, it will be noted that during training time of the ML model, the output from the RNN model is compared with the freshness index/quotient at time t, where freshness index/quotient refers to a label provided by an expert, to determine the loss of the model at time t. This loss may be back-propagated to update the weight ($W_s$) and bias ($b_s$) terms of the model.

Prior to feeding the visual data/input, which includes a training dataset comprising food images captured by a high resolution camera, to the RNN model, said food images are fed to a pre-trained Convolution Neural Networks (CNN). The CNN network extracts features from the images using a technique called transfer learning. Using the training dataset of food images, the pre-trained CNN network generates the first vector embedding for said food images at 606. The first vector embedding provides unique visual representations of the food items taking in to consideration the low level image features such as color, texture, and so on; mid-level features such as shapes, edges, and so on; and high resolution features such as objects which are part of the food images.

A single weight shared CNN network can be used across the time instances of the RNN model. Weight sharing allows the same parameters to be updated using a back-propagated loss at each time instance.

For instance, at time instance t the first vector embedding representing image feature vector is represented as it and the second vector embedding representing sensory data is represented by as $s_t$. The first vector embedding is concatenated with the second vector embedding to obtain a concatenated vector embedding at the time-instance t (at 608 of FIG. 6). Thus, $x_t = [i_t, s_t]$ where, [,] indicates concatenation of the first vector embedding and the second vector embedding and $x_t$ is the input to the $t^{th}$ time instance of RNN network.

Said pre-trained CNN network is fine-tuned while training the RNN model with the time series data. Fine-tuning involves using the weights and biases of the pre-trained CNN network as the point of initialization and then updating those further during training of the entire model (randomly initialized RNN model and pre-trained CNN model) back-propagating the loss computed at the output of the RNN network. For example, the CNN model is pre-trained on a generic food data as a simple classification model. Such a CNN model that is pre-trained on the generic data associated with the food items may hereinafter be referred to as a pretrained CNN model. The pre-trained CNN model is used in the system architecture 500. The same pre-trained CNN model is used across the input time instances (for instance, t−1, t, t+1, and so on) of the RNN model. As a part of training of the RNN model, the pre-trained CNN model is fine-tuned, and a plurality of weights of the pre-trained CNN model are updated by the gradients obtained from each of the input time-instance of the RNN model. Herein, since the same pre-trained CNN model is used across the multiple input time-instances and during the process of training of the ML model, the CNN model is fine-tuned when the plurality of weights thereof are updated during the backpropagation step, by the gradients obtained from each of the multiple input time-instance, the CNN model is called as shared weight CNN model.

Herein, it will be understood that the advantage of taking the visual input along with the sensory data is two-fold: (i) Sensory data explicitly captures the parameters which are contributing towards food freshness, however there can be some unknown (implicit) visual parameters which may be contributing to depict the freshness of the food. For example, black dots on banana or change of color of mango, and so on. By taking the image data along with the sensory data, the system 500 enables capturing the implicit visual characteristics which are contributing towards the freshness of the food. Rate of change of these characteristics is captured by using a time series model (RNN). The combination of explicit characteristics captured through sensory data and implicit characteristics modeled and captured using visual data leads to enhanced accuracy in determining the freshness of food items.

Fine tuning of said shared weight CNN network during the training of ML model provides an updated visual representation (embedding) of the food item (image) at its output (it). Due to the process of fine-tuning, which has the objective of predicting the freshness of the food-item at every time instance, the embedding generated through the fine-tuned CNN model takes into consideration the effect of the freshness prediction at that as well as all prior time instances, for example, at time instance t−1, time-instance t, time-instance t+1, and so on. After training of the ML model along with fine-tuning of the underlying shared CNN network, the CNN network separately can be used to provide embedding of images of food items. Said embedding may demonstrate the freshness of the food item, more specifically, the visual representations which depict freshness of the food item, for example, black dots on banana or change of color in case of mangoes, etc. When this CNN model is fed with the images which are marked as 'ideal for use' from freshness perspective, vectorized representation at the output of the CNN model provides a digital signature of that food item from freshness perspective. The average of multiple of such representations for multiple of images of 'ideal' food items defines the standardized digital signature depicting ideal freshness quotient. The embeddings provided by the trained CNN model for images of distinct food items can be compared with this standardized representation using vector similarity measures to depict their idealness for use from freshness perspective.

Figure 7A:
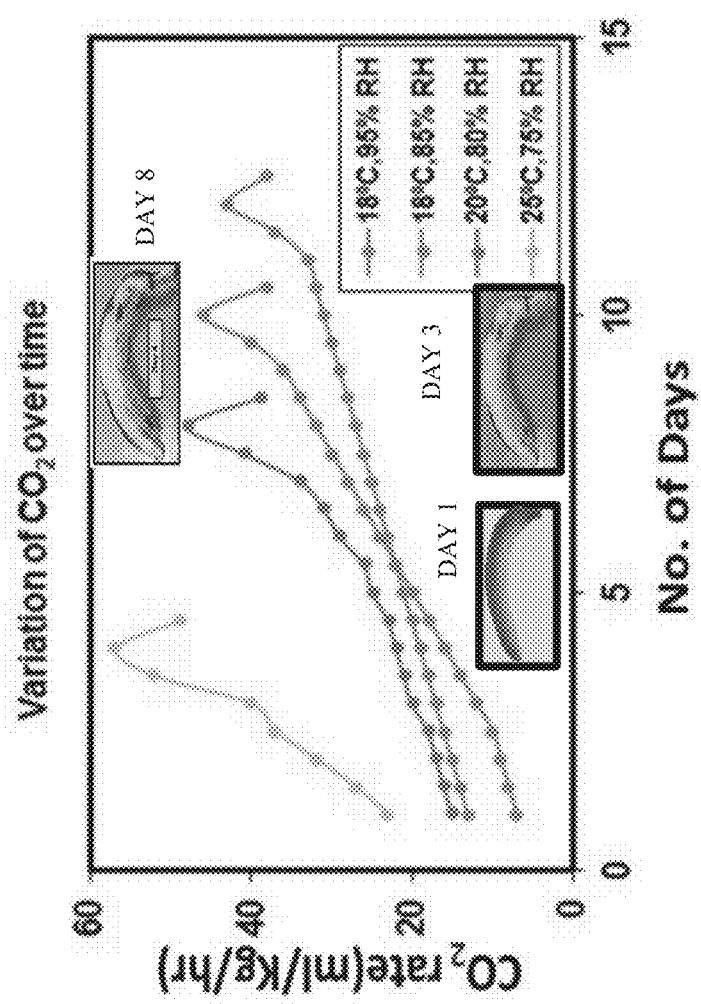
FIGS. 7A-7C illustrate an example scenario for monitoring and quality evaluation of perishable food items and prediction of shelf life thereof, according to some embodiments of the present disclosure.
Figure 7B:
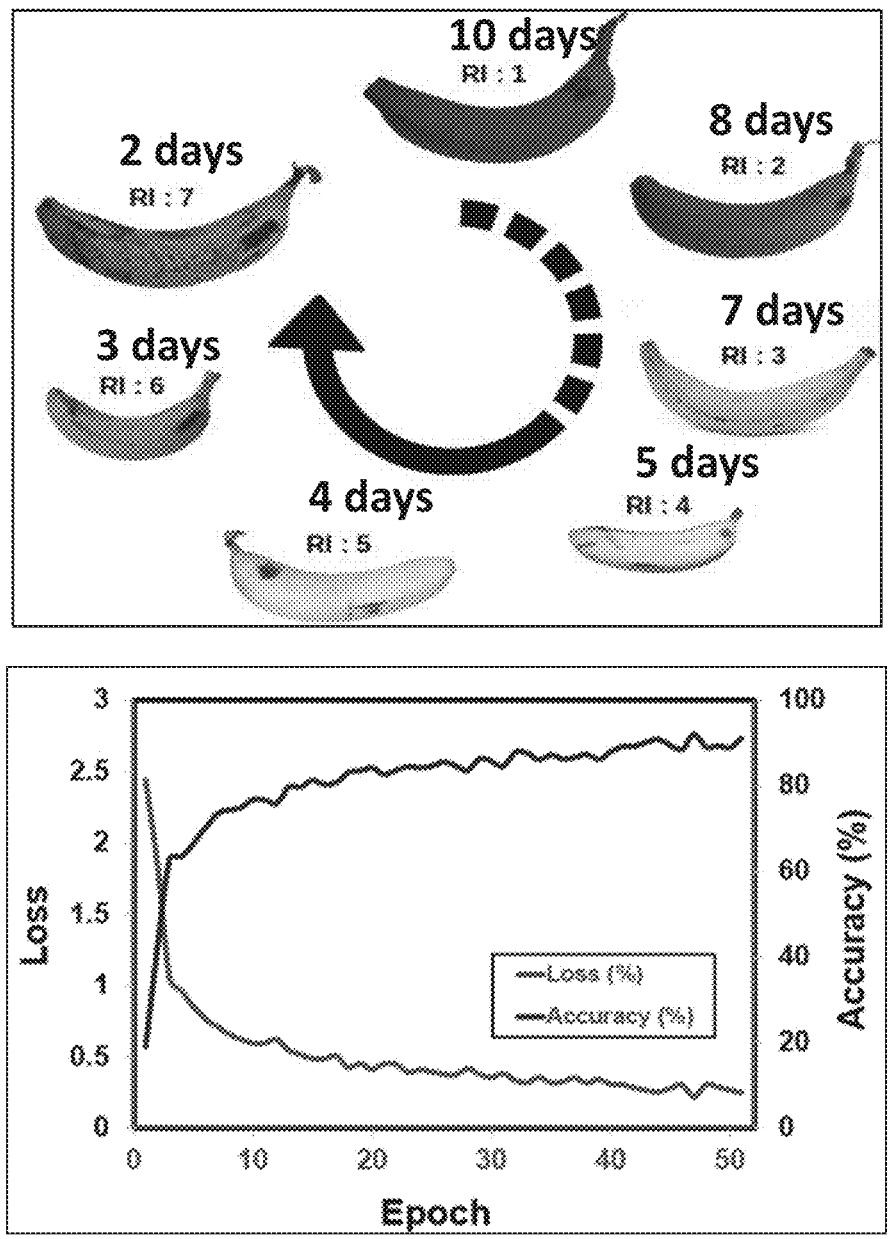
Figure 7C:
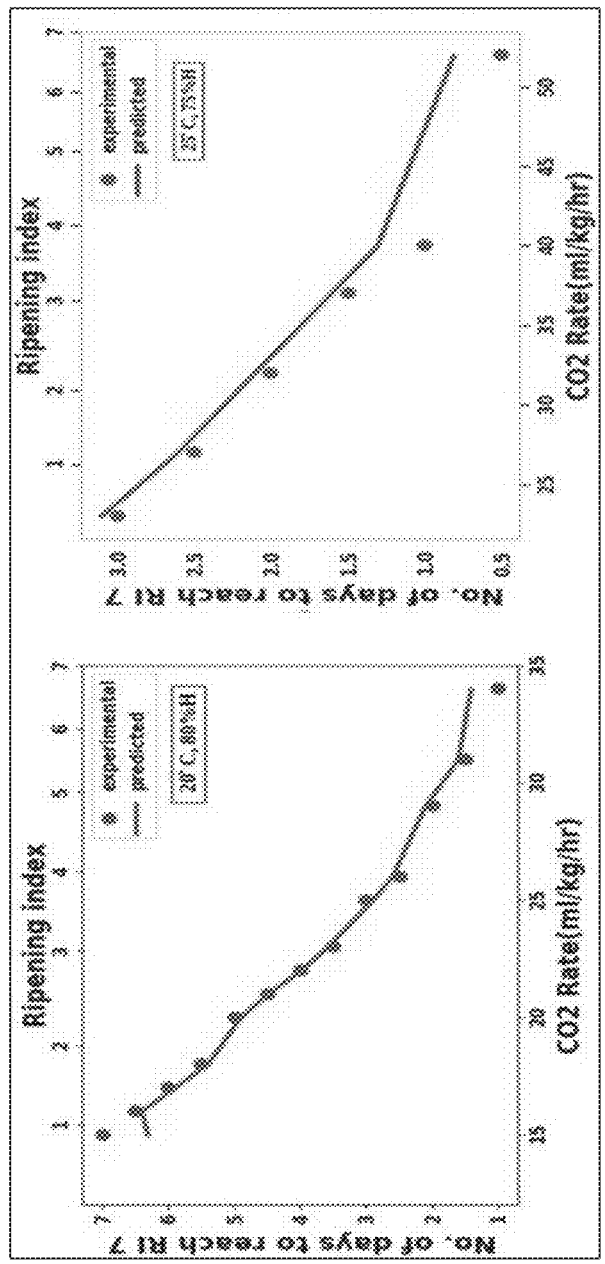

An example scenario describing shelf life study of food items, and mathematical model therefor is described further with reference to FIGS. 7A, 7B and 7C.

Example Scenario:

In an example scenario, the shelf life study of food items has been carried out and mathematical models are developed to predict the shelf life of these food items. Example of the shelf life study performed with banana is shown in FIG. 7A. As seen in FIG. 7A, bananas are stored at different environmental conditions to mimic the variations in temperature and humidity during different seasons, different geographies and different conditions in the storage house. The experiments were performed at 1) Temperature 20° C., Relative humidity (RH) 80% 2) Temperature 25° C., RH 75% 3) Temperature 18° C., RH 85% 4) Temperature 18° C., RH 95%. It has been observed that the bananas stored at 18° C. and 95% RH have shown maximum shelf life among the bananas kept in other environmental conditions. This was found as bananas when stored at lower temperature and higher humidity conditions, respiration rate is less, the bananas ripens at a slower rate and hence has a larger shelf life. It has also been observed that the bananas stored at 25° C. and 75% RH have shown minimum shelf life among the bananas kept in other environmental conditions as they were kept at higher temperature and lesser humidity conditions. It was also observed, the shelf life of the bananas kept at 18° C. and 85% RH has a longer shelf life compared to bananas kept at 20° C. and 80% RH. However the bananas kept at 18° C. and 85% RH has a shorter shelf life compared to bananas kept at 18° C. and 95% RH due to lesser humidity conditions. The developed platform has provision to use the data based and Image based models to predict the shelf life of the food items. These models can predict the shelf life in terms of at least one of the shelf life defining parameter such as weight loss, change in colour, change in texture, change in gaseous parameters sugar content and the quality of the processed food prepared from the agricultural food item. For example, the quality of chips prepared from bananas stored at different conditions.

FIGS. 7B-7C illustrates experimental and predicted shelf life based on the calculated respiration rate, ripening stage in accordance with the example scenario.

Various embodiments disclose method and system for monitoring and quality evaluation of perishable food items. Freshness of perishable food items and/or shelf-life thereof is determined as a function of many multivariate, mutually exclusive varying parameters via an intelligent model. The system enables developing continuous controlled monitoring technique by recreating the environmental conditions present at source, during transit or storage, in the custom enclosed chamber to predict freshness of perishable food items at source, during transit and storage. The disclosed framework may be able of controlling the environmental conditions in the enclosed chamber containing food item to maintain the favorable conditions surrounding the food items.

An important contribution of the disclosed embodiments is determination of freshness of the food item in quantitative terms. In an embodiment, the quantitative determination of freshness of the food items is based on receipt of sensor data as well as visual data pertaining to the food items. Inclusion of visual contents using CNNs fine-tuning provides updated visual embedding of the food item, which is a vectorized representation of the food item that depicts visual freshness characteristics thereof. In an embodiment, the disclosed system can be used to develop Internet of Things (IoT) platform, in which the synchronized data output obtained at specified intervals can be interfaced with cloud/Personal Computer (PC). The quantified data can be displayed on a mobile screen, iPad, tablets and so on, through cloud/Wi-Fi module/gsm-module.

Figure 8:
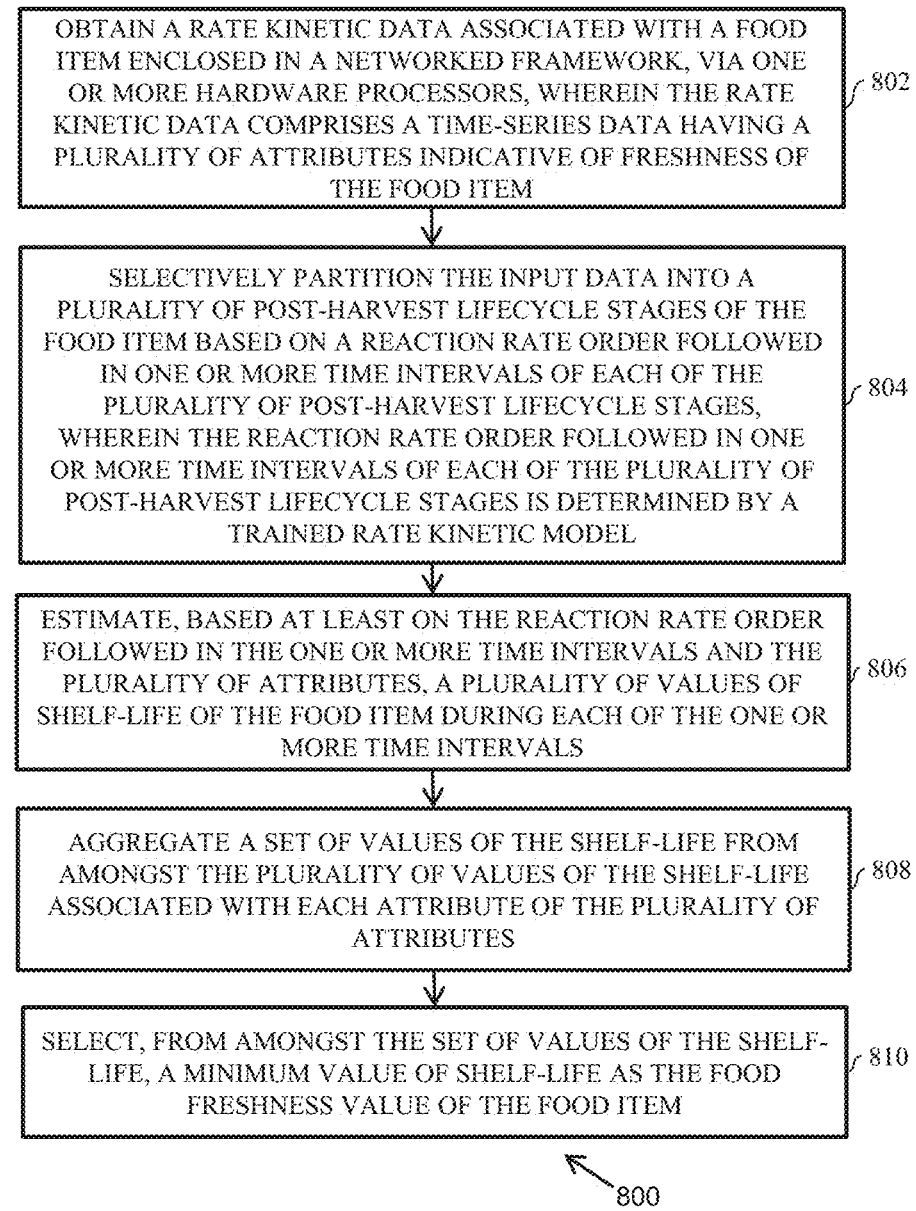
FIG. 8 illustrates an example flow diagram depicting a method for monitoring and quality evaluation of perishable food items, in accordance with another example embodiment.

In another embodiment, the monitoring and quality evaluation of the of perishable food items can be performed by a system incorporating a rate kinetic model, as described further with reference to FIGS. 8 through 11N. For example, FIG. 8 illustrates an example flow diagram depicting a method for monitoring and quality evaluation of perishable food items, in accordance with another example embodiment. FIGS. 9A-9B illustrates an example flow diagram depicting a method for monitoring and quality evaluation of perishable food items, in accordance with another example embodiment. FIGS. 10A-10K illustrate an example scenario for monitoring and quality evaluation of perishable food items and prediction of shelf life thereof, according to some other embodiments of the present disclosure.

FIG. 8 illustrates an example flow-diagram of a method 800 for monitoring and quality evaluation of perishable food items, using the system described with reference to FIGS. 1-3, in accordance with example embodiments of the present disclosure. The steps of the method 800 of the present disclosure will now be explained with reference to the system 102 as depicted in FIG. 1 or the system 300 as depicted in FIG. 3, and the steps of flow diagram as depicted in FIG. 8. The system 102/300 includes one or more data storage devices or the memory 304 operatively coupled to the processor(s) 302, and is configured to store instructions for execution of steps of the method 800 by the processor(s) 302.

Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

At 802, method 800 includes obtaining a rate kinetic data associated with a food item enclosed in a networked framework, via one or more hardware processors. In an embodiment, the rate kinetic data may include sensory data. In an embodiment, the rate kinetic data may include one or more of weight of the food item, weight loss of the food item, moisture content in the food item, moisture loss during the storage, concentration of specific compound in the food item, and concentration of specific gas such as Carbon dioxide (CO2), ethylene (C2H4,), ammonia (NH3) released by the food item. Additionally, the rate kinetic data may include a visual data having images of the food item. The visual data may be received based on the monitoring of the food item from the networked framework, for example networked framework 200 (FIG. 2). For example, in an scenario, sprouting may be as one of the attributes of the plurality of attributes that may be measured in terms of percentage area covered on the food item. In such a scenario, the visual data pertaining to the sprouting of the food item may be obtained from image sensors associated with the networked framework, and further may be utilized for shelf-life determination.

Herein, it will be understood that said networked framework (illustrated and described previously with reference to FIG. 2) is capable of incorporating multiple mutually exclusive sensors, including but not limited to, pH sensor, optical sensor, gas sensor (for instance, $O_2$, $CO_2$, $NH_3$, methane, ethylene, and so on), temperature sensor, humidity sensor, weighing sensor, color sensor, NIR sensor with micro spectrophotometer, ultrasonic sensor, GSR sensor, and so on integrated inside a customized enclosure capable of periodic, synchronized data logging corresponding to the food item. Herein, the ultrasonic sensor measures any new growth by using ultrasonic waves, NIR sensor with micro spectrophotometer obtains spectra of sub-micron levels, the GSR sensor suitably modified as per requirements measures minute, delicate changes with respect to skin resistance of the perishable item which perhaps mark the beginning of degradation and cannot be measured otherwise.

In an embodiment, said mutually exclusive sensors may be integrated in a smart plate embodying the networked framework 200. The aforementioned networked framework 200 enables multivariate sensing and monitoring of perishable food items like fish, meat, dairy products, post-harvest fruits, vegetables and other perishable food items. In an embodiment, the sensors may include a modular configuration, and hence may be replaced based upon the food item. The food items may also be illuminated by various frequencies of light. In an embodiment, the disclosed framework may be a modular framework where any existing sensor can be removed or any new sensor can be plugged in as per requirements. Also, multiple sensors and multiple cameras may be installed inside a custom enclosure embodying the networked framework with parameter variation control such as, but not limited to, temperature, humidity, and so on to capture periodic changes in the food item from all directions depending upon the requirements. Herein, it will be understood that the disclosed networked framework is capable of automatically activating only those sensors from amongst a plurality of aforementioned sensors to which the food item responds. Depending on the choice of the food item, one or more sensors can be invoked and that model can be used for prediction of freshness of the food. For example, cheese may require pH sensor while fruits may require Ethylene and $CO_2$ sensors for monitoring. The networked framework for monitoring the food items and capturing the sensory data and the visual data therefrom is further described in the Indian Patent application no. 201821040783 titled, "Integrated Framework for Multimodal Sensing and Monitoring of Perishable Items" and is incorporated herein by reference.

In an embodiment, the method includes collecting the visual data and the sensory data using at least one of an invasive and a non-invasive technique. The invasive techniques include use of laboratory methods to calculate different food compositional parameters including at least one of sugar, starch, fat, protein, vitamins and antioxidants. The non-invasive technique may, but are not limited to, use of non-invasive sensors, such as gas sensors, acoustics, optical sensors, near infrared sensor, and so on.

In an embodiment, the method 800 includes defining one or more attributes that may be the parameters defining the shelf-life of the food item. For example, a change in weight (g) may be defined as an attribute for determining shelf-life of the food item. In an embodiment, the rate of change of the attributes may be a time-series data and may hereinafter be referred to as rate kinetic data for the purpose of description of the disclosed embodiments.

In an embodiment, a profile for change in value of attribute with time from t=0 to t=n may be plotted, and after different step-intervals ($t_{step}$) or time intervals the value of attributes is collected. Here, n is the total number of time intervals under which data is collected.

In an embodiment, the disclosed method includes receiving the rate kinetic data, for example the sensory data and optionally the visual data, from the integrated networked framework in real-time, and monitoring the food item to further estimate a degree of freshness/quality/shelf-life of the food item therefrom. The method utilizes a trained rate kinetic model and a plurality of attributes associated with the shelf-life of the food-item. The trained rate kinetic model may be pre-trained using a training data including multivariate, multi-parameter, multi-modal sensory as well as visual data associated with the food items. In an embodiment, the training data may be iteratively fitted on to reaction rate equations, for example, a zero order, a first order and a second order reaction rate equations in that order to obtain the trained rate kinetic model for the food item.

At 804, method 800 includes selectively partitioning the input data or the rate kinetic data into a plurality of post-harvest lifecycle stages of the food item based on a reaction rate order associated with one or more time intervals of each of the plurality of post-harvest lifecycle stages. The reaction rate order associated with the one or more time intervals refers to the reaction rate order followed in those one or more time intervals of each of the plurality of post-harvest lifecycle stages, and is determined by the trained rate kinetic model. In an embodiment, the rate kinetic data is converted into the time-series data into an integrated form of zero, first and second order rate reaction equations in a sequential order to obtain a plot of rate of change of concentration terms associated with the rate kinetic model. Herein, the concentration terms for the zero order, the first order and the second order reactions may be ($C_0$–C), $\ln(C/C_0)$, ($1/C$–$1/C_0$), as will be described further with reference to FIGS. 9A-9B. Herein, for a time interval t-t0, C represents the value of attribute at time t, and C0 represents the value of attribute at time t0.

Further, a value of coefficient of determination is obtained from the plot of integral form of the zero, first and second order reactions in the sequential order. The order of reaction is determined based on a comparison of the value of the coefficient of determination with a threshold value of the coefficient of determination. Herein, the order of the reaction is indicative of a nature of reaction responsible for biochemical changes in the food item during the post-harvest lifecycle stage of the food item. The selective partitioning of the rate kinetic data and determination of the order of reaction for each of the time intervals is described further in detail with reference to the flow-diagram of FIGS. 9A-9B.

At 806, the method 800 includes estimating, based at least on the reaction rate order followed in the one or more time intervals and the plurality of attributes, a plurality of values of shelf-life of the food item during each of the one or more time intervals, via the one or more hardware processors. At 808, the method 800 includes aggregating a set of values of the shelf-life from amongst the plurality of values of the shelf-life associated with each attribute of the plurality of attributes, via the one or more hardware processors. At 810, the method 800 includes selecting, from amongst the set of values of the shelf-life, a minimum value of shelf-life as the food freshness value of the food item, via the one or more hardware processors. Herein, the order of the reaction depicts the nature of the reaction responsible for biochemical changes in the food item during said post-harvest stage of the food item. Said order of reaction may be utilized to identify appropriate environmental conditions required during the storage of the food items. For example, different reactions responsible for the biochemical changes (e.g. weight loss in the present embodiment) are transpiration and respiration. During the first stage of the plurality of post-harvest life cycle stages of the food item, high value of rate constant indicates the transpiration and the relatively lower rate constant in the second stage indicates dominance of respiration rate in that stage. Hence, in order to prevent the weight loss during first stage, there is a need to reduce the transpiration, which can be achieved by keeping the food item (for example, potato) in high relative humidity environment, whereas during the second stage, in order to reduce the weight loss there is a need to reduce the respiration rate, which can be achieved by keeping the food item at low temperatures and high humidity. In another embodiment, the order of reaction may be utilized for determination of remaining shelf-life of the food item.

Figure 9A:
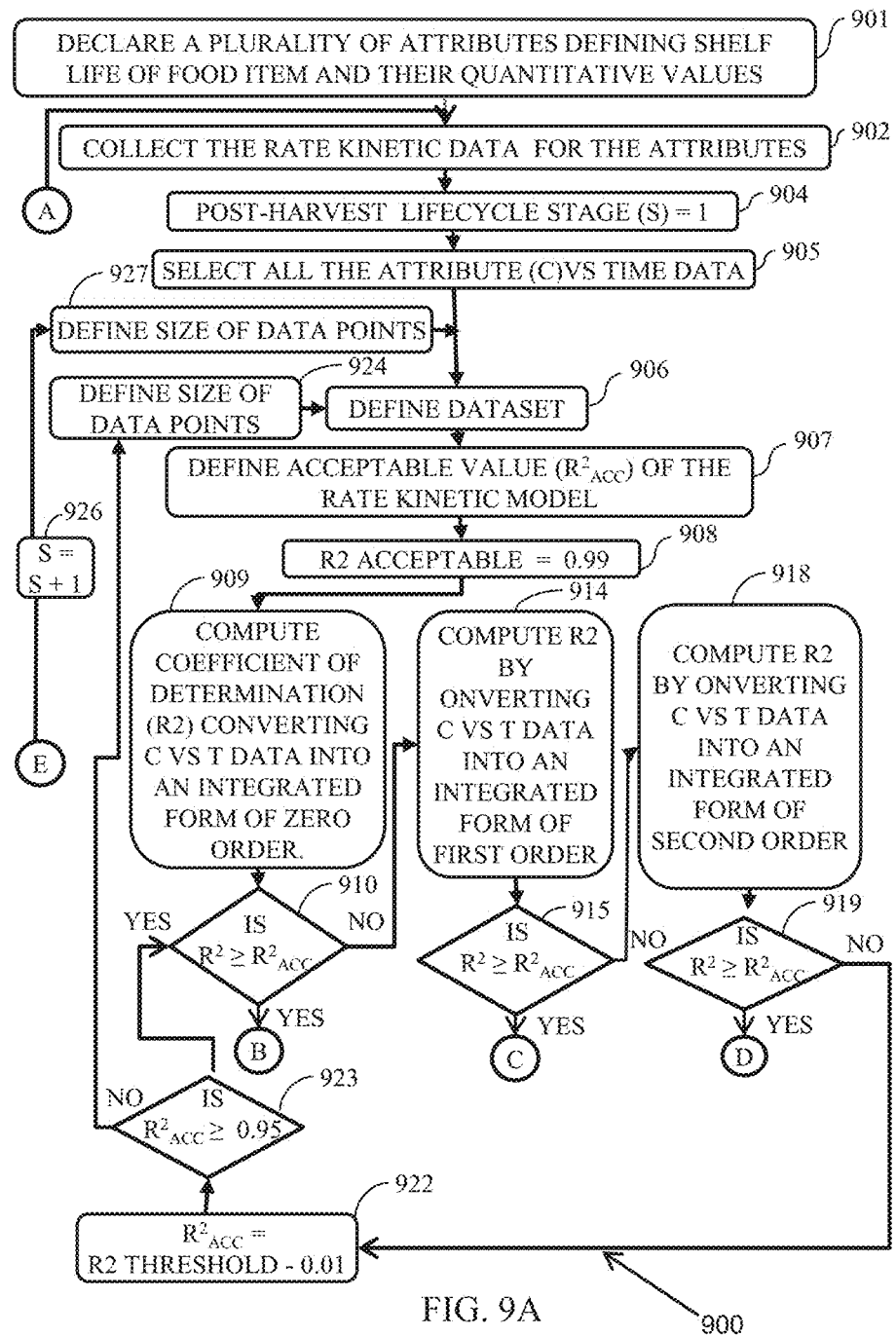
FIGS. 9A-9B illustrates an example flow diagram depicting a method for monitoring and quality evaluation of perishable food items, in accordance with another example embodiment.
Figure 9B:
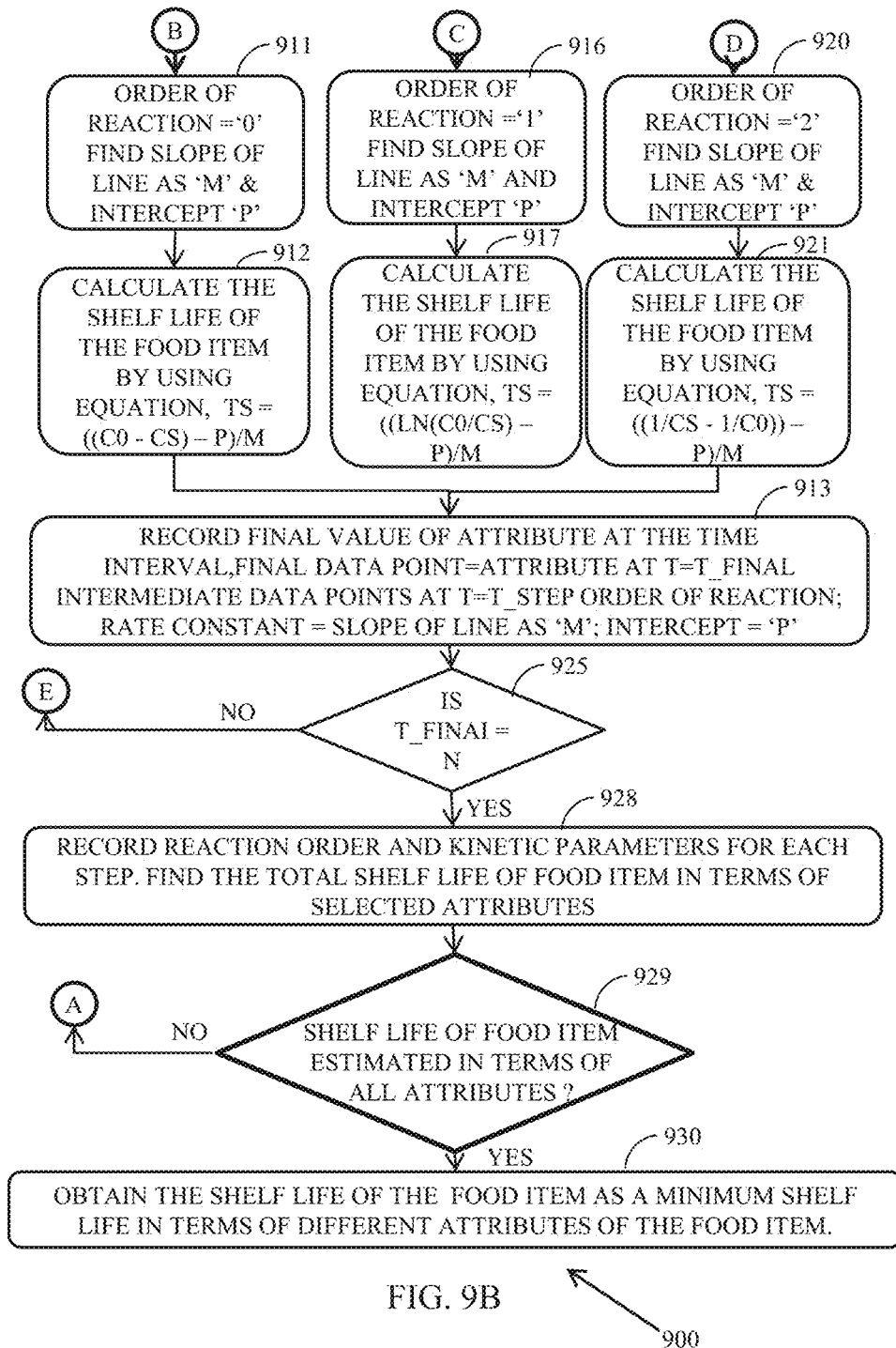

FIGS. 9A-9B illustrate an example flow-diagram of a method 900 for monitoring and quality evaluation of perishable food items, using the system described with reference to FIGS. 1-3, in accordance with example embodiments of the present disclosure. The steps of the method 900 of the present disclosure will now be explained with reference to the system 102 as depicted in FIG. 1 or the system 300 as depicted in FIG. 3, and the steps of flow diagram as depicted in FIGS. 9A-9B. The system 102/300 includes one or more data storage devices or the memory 304 operatively coupled to the processor(s) 302, and is configured to store instructions for execution of steps of the method 800 by the processor(s) 302.

Although process steps, method steps, techniques or the like may be described in a sequential order, such processes, methods and techniques may be configured to work in alternate orders. In other words, any sequence or order of steps that may be described does not necessarily indicate a requirement that the steps to be performed in that order. The steps of processes described herein may be performed in any order practical. Further, some steps may be performed simultaneously.

As described previously with reference to FIG. 8, the attributes defining the shelf-life of the food item, and values thereof are declared at 901. The rate kinetic data or rate of change of said attributes with time is obtained in terms of time-varying data by monitoring said attributes using the networked framework at 902.

The rate kinetic data is selectively partitioned into a plurality of post-harvest lifecycle stages of the food item based on a reaction rate order followed in one or more time intervals of each of the plurality of post-harvest lifecycle stages at 903. For identification of post-harvest lifecycle stages of the food item, at an initial stage (or stage 1) at 904, a count of stages is initialized to one. All the time series data (i.e. time vs attribute data) is selected at 905, and a dataset is defined therefrom at 906. For example, a dataset having an initial point, intermediate points, and a final point is initialized. In an embodiment, the Initial point=Attribute value at time t=t_initial; the Intermediate points=Attribute value at time intervals between t=t_initial to t=t_final varied at time interval of t_step; and the Final point=Attribute value at t=t_final days may be initialized.

The dataset is selectively partitioned into a fixed number of logical stages into a plurality of post-harvest lifecycle stages in a holistic manner by understanding the reaction rate order it follows in the specific time intervals, as will be described further. In an embodiment, the start time, the gap between two time intervals, and the final time interval may be initialized respectively as 't_initial'=Start time; tstep=the gap between two time intervals, t_final=the final time interval. For example, in one scenario, said attribute data may be initialized as t_initial=0 days, t_step=1 days, t_final=n days.

At 907, the method 900 includes defining the required accuracy/fitness of the rate kinetic model measured in terms of $R^2$. At 908, a threshold value of coefficient of determination ($R^2$) is defined. In an example scenario, the threshold value of coefficient of determination ($R^2$) is defined as 0.99. At 909, the time-series data (namely, the rate of change of attribute C vs t data) is converted into an integrated form of zero order, and a concentration term of integrated form of zero order ($C_0$–C) vs time is plotted. A straight line passing through origin is fit and the $R^2$ value is determined. At 910, it is determined whether $R^2$ is greater than or equal to $R^2_{acceptable}$. If it is determined at 910 that $R^2$ is greater than or equal to $R^2_{acceptable}$, then at 911, order of the reaction='0'=zero order, and slope of line is determined as 'm' and intercept as 'p'. Further, at 912, the shelf life of the food item is calculated by using equation, $t_s = ((C_0 - C_s) - p)/m$, where $C_s$ is the value of attribute at the end of shelf life. At 913, final reading may be recorded as Step=Step, Initial data Point=Attribute at t=t_initial, Final data point=Attribute at t=t_final, Intermediate data points at t=t_step, Order of reaction='0'; Rate constant=slope of line as 'm'; Intercept='p'.

If it is determined at 910 that the value of coefficient of determination $R^2$ is less than $R^2_{acceptable}$, then at 914, the C vs t data is converted into an integrated form of first order, and concentration term $\ln(C/C_0)$ vs time is plotted. Further, a straight line passing through origin is fitted and the $R^2$ value is determined. It is further determined at 915, whether $R^2$ is greater than or equal to $R^2_{acceptable}$. If it is determined at 915 that $R^2$ is greater than or equal to $R^2_{acceptable}$, then at 916, order of reaction='1'=First order, the slope of line is determined as 'm' and the intercept is determined as 'p'. Further, at 917, the shelf life of the food item is calculated by using equation, $t_s=((\ln(C_0/C_s)-p)/m$, where $C_s$ is the value of attribute at the end of shelf life. The method at 917 is followed by 913, where the final reading may be recorded, as described above.

If however, it is determined at 915 that $R^2$ is less than $R^2_{acceptable}$, then at 918, the C vs t data is converted into an integrated form of second order. The concentration term of second order $(1/C-1/C_0)$ vs time is plotted, a straight line passing through origin is fitted, and the coefficient of determination $R^2$ value is determined. Further at 919, it is determined whether $R^2$ is greater than or equal to $R^2_{acceptable}$. If it is determined at 919 that $R^2$ is greater than or equal to $R^2_{acceptable}$, then at 920, order of reaction='2'=second order, the slope of line is determined as 'm' and the intercept is determined as 'p'. Further, at 921, the shelf life of the food item is calculated by using equation, $t_s=((1/C_s-1/C_0)-p)/m$, where $C_s$ is the value of attribute at the end of shelf life. The method at 921 is followed by 913, where the final reading may be recorded, as described above.

If however, at 919, it is determined that $R^2$ is less than $R^2_{acceptable}$, then $R^2_{acceptable}$ is equated to $R^2_{acceptable}-0.01$ at 922, followed by a determination at 923 (till the value of $R^2_{acceptable}$ reaches to 0.95), where the threshold value of $R^2 \geq 0.95$. If it is determined at 923 that the threshold value of $R^2$ is greater than or equal to 0.95, then the method 900 follows from 910 again, where the value of coefficient of determination is updated and subsequent steps are followed for identifying a post-harvest stage of the food item. If however, it is determined that the threshold value of the coefficient of determination $R^2$ is less than 0.95, then at 924, Size of the data points is updated as nsize=nsize-1, t_initial=t_initial days, t_step=t_step days, and t_final=t_final-t_step days, and the dataset is defined at 906. Thereafter, the method 900 follows from 906 again.

As described above, the method 900 from 912, 917, and 921 follows after method at 925. At 925, it is determined whether all of the one or more time intervals associated with a post-harvest life cycle stages of the food item have been accessed/considered, i.e.. t_final=n. If it is determined at 925 that all of the time-intervals have not been considered, i.e. t_final is not equal to n, then at 926 the count of stage is increased by one. At 926 the size of the data points nsize=n−t_final, t_initial=t_final days, t_step=t_step days, and t_final=n days. and the dataset is defined at 906. Thereafter the method 900 follows from 906 again.

If however at 925 it is determined that all of the time-intervals have been considered, i.e. t_final=n, then at 928 the reaction order and rate kinetic parameters for each step are recorded at 928. For example, for Stage 1, Data size (time interval, attribute value), reaction order, rate constant are recorded; for Stage 2, Data size (time interval, attribute value), reaction order, rate constant are recorded; and for Stage n, Data size (time interval, attribute value), reaction order, rate constant are recorded.

Based at least on the reaction rate order followed in the one or more time intervals and the plurality of attributes, a plurality of values of shelf-life of the food item are determined during each of the one or more time intervals. In an embodiment, a set of values of the shelf-life are from amongst the plurality of values of the shelf-life that are associated with each attribute of the plurality of attributes, are aggregated. For example, the total shelf life of food item is determined in terms of selected attribute (e.g. weight loss, moisture loss, etc.). Also, total Shelf life=ts_stage1+t_stage2+t_stage n.

Further at 929, it is determined whether the shelf life of food item is estimated in terms of all attributes. If it is determined at 929 that the shelf life of food item is not estimated in terms of all attributes, then the method 900 follows from 902 to collect the rate kinetic data for the attributes. If however, it is determined at 929 that the shelf life of food item is estimated in terms of all attributes, then at 930 the shelf life of selected food item is declared. At 810, method 800 includes selecting, from amongst the set of values of the shelf-life, a minimum value of shelf-life as the food freshness value of the food item, as presented in the expression below:

Shelf life=minimum (Total shelf life_attribute 1, Total shelf life_attribute 2, . . . Total shelf life_attribute n)

Figure 10A:
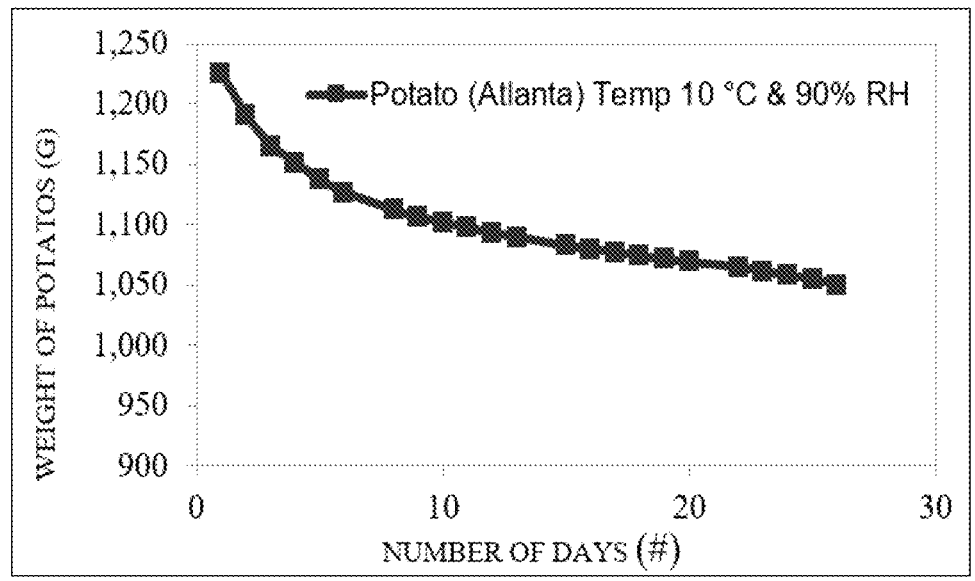
FIG. 10A illustrates variation of weight of potatoes plotted against time, in accordance with an example embodiment.

An example illustrating determination of the plurality of post-harvest lifecycle stages of the food item is described further with reference to FIGS. 10A-10K, in accordance with an example embodiment of the present disclosure. In the present example scenario, said stages have been determined by taking an example of the food item, potato (variety Atlanta), as shown in FIG. 10A. The potatoes are stored at different environmental conditions for a number of days to mimic the variations in temperature in the storage house. During the time of storage, the weight of potatoes is monitored, as is shown in Table-I below.

TABLE I

Time-series data of variation of food attribute with time

| Time Number of days | Attribute Weight of potatoes (g) |
|---|---|
| 1 | 1225.2 |
| 2 | 1190.2 |
| 3 | 1164.6 |
| 4 | 1151.3 |
| 5 | 1137.0 |
| 6 | 1126.4 |
| 7 | |
| 8 | 1112.0 |
| 9 | 1106.0 |
| 10 | 1101.7 |
| 11 | 1097.5 |
| 12 | 1093.0 |
| 13 | 1089.1 |
| 14 | |
| 15 | 1082.7 |
| 16 | 1079.5 |
| 17 | 1076.8 |
| 18 | 1073.7 |
| 19 | 1071.5 |
| 20 | 1069 |
| 21 | |
| 22 | 1064.7 |
| 23 | 1061.2 |
| 24 | 1057.8 |
| 25 | 1054.9 |
| 26 | 1049.7 |

At an initial stage (or stage 1), entire data, for example the data given in table-I is considered. Said data is plotted against time to obtain the rate kinetic data (or time series data), as shown in FIG. 10A. As a next step, the C vs t data is converted into an integrated form of zero order, and the concentration terms of integrated form of zero order $(C-C_0)$ vs time graph is plotted. From the rate kinetic data, a zero order reaction rate equation is obtained, as illustrated in FIG.

Figure 10B:
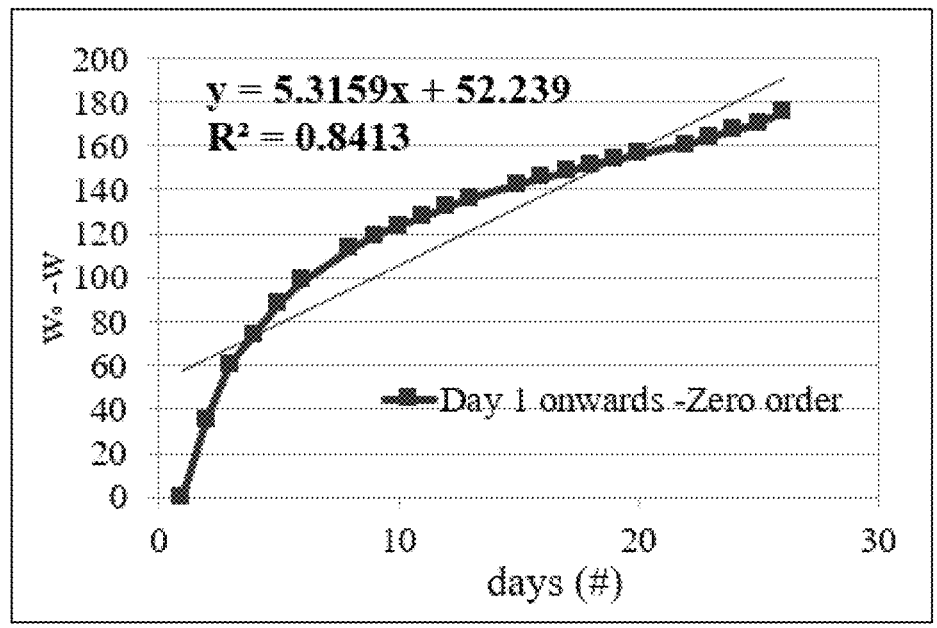
FIGS. 10B-10D illustrates rate kinetic data to obtain a zero-order reaction rate equation, a first order reaction rate equation and a second order reaction rate equation, respectively in accordance with an example embodiment.
Figure 10C:
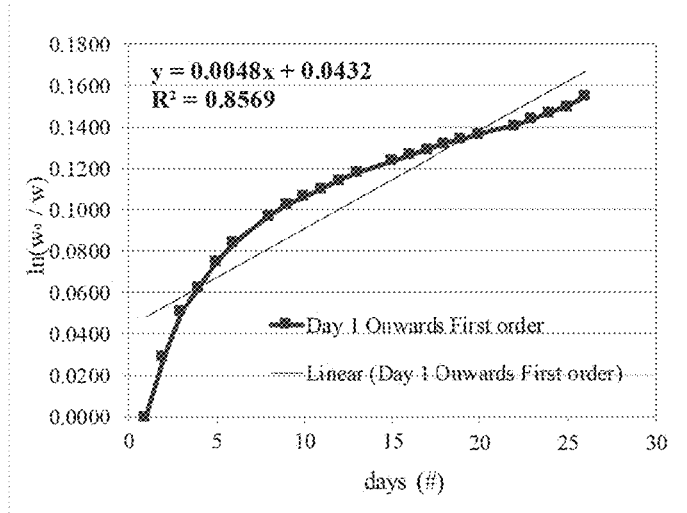
Figure 10D:
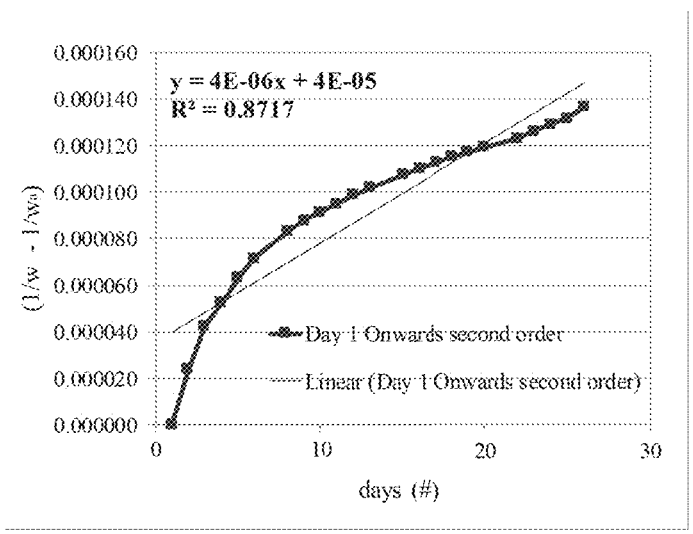
Figure 10E:
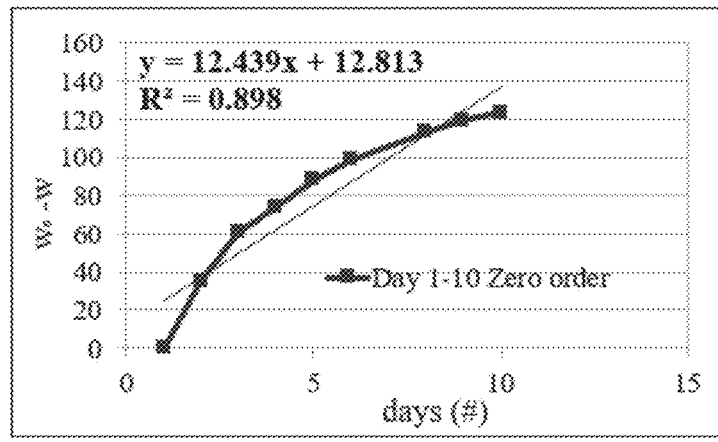
FIGS. 10E-10G illustrates rate kinetic data to obtain a zero-order reaction rate equation, a first order reaction rate equation and a second order reaction rate equation, respectively in accordance with another example embodiment.
Figure 10F:
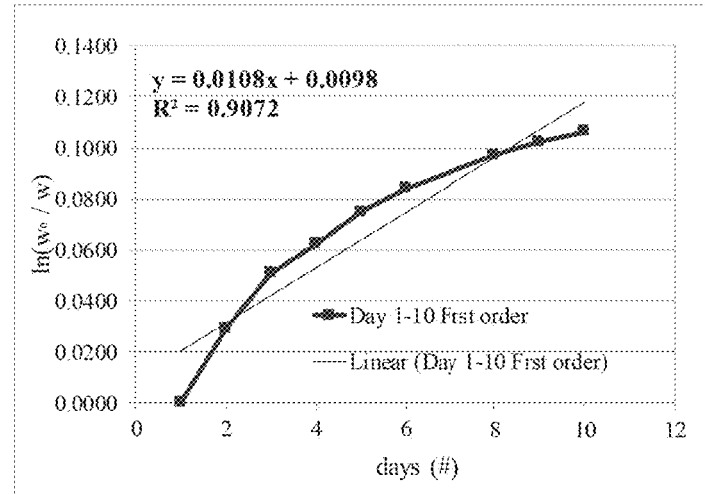
Figure 10G:
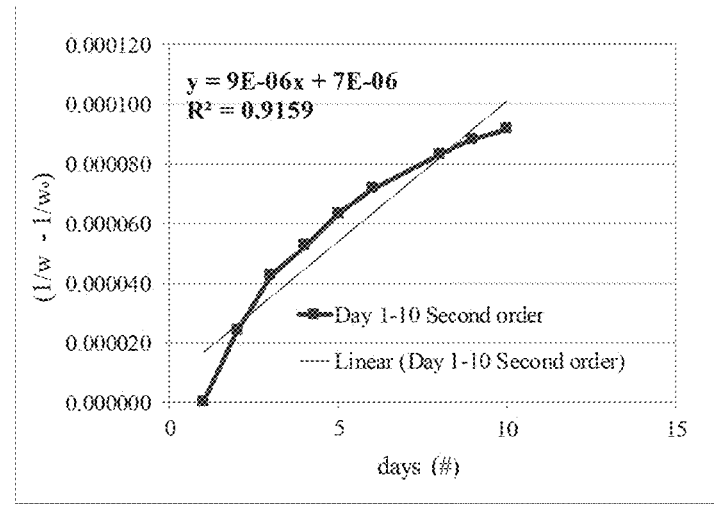
Figure 10H:
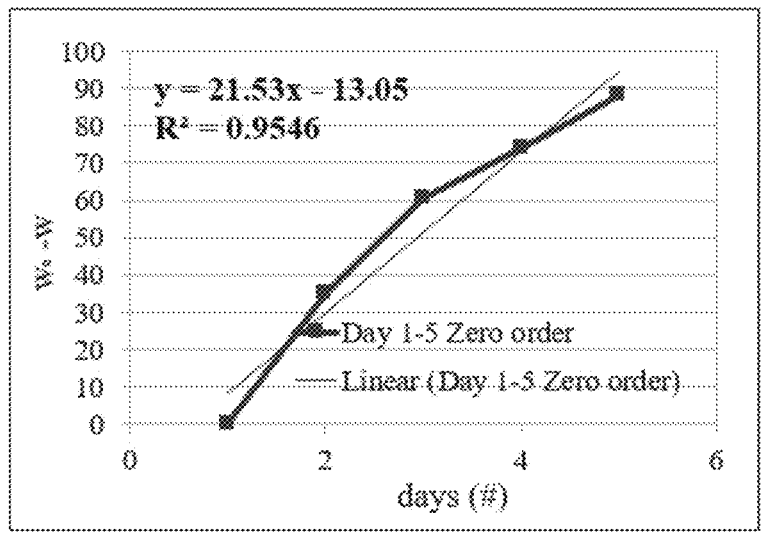
FIGS. 10H-10J illustrates multistage rate kinetic models (combined first stage and second stage) in accordance with another example embodiment.

10B. Moreover, a value of coefficient of determination is computed. For example, in the stage 1, where entire data is considered in one stage, the value of coefficient of determination ($R^2$) is 0.8413 (FIG. 10B). In an embodiment, the value of coefficient of determination is computed by using the equation:

$$R^2 = \frac{\sum_{i=1}^{n}(y_i - \hat{y}_i)^2}{\sum_{i=1}^{n}(y_i - \bar{y})^2}$$

Where $y_i$ is the attribute value from time t=0 to t=n, $\hat{y}_i$ is the predicted value of the attribute and $\bar{y}$ is the mean of the actual food attribute data Herein, the value of $R^2$ is determined to be less than the threshold value of coefficient of determination (which is 0.95). Hence as a next step, the C vs t data is converted into an integrated form of first order, and the $\ln(C/C_0)$ vs time graph is plotted. A straight line passing through origin is fit through the graph and the $R^2$ value is determined. The graph is illustrated in FIG. 10C. As is seen form FIG. 10C, the value of coefficient of determination is 0.89, which is less than the threshold value. Hence, the C vs t data is converted into an integrated form of second order, and the $(1/C-1/C_0)$ vs time is plotted as shown in FIG. 10D. A straight line passing through origin is fitted and again the $R^2$ value is computed. As seen from FIG. 10D, the value of $R^2$ is determined to be less than the thresholds value of 0.95. Hence the dataset is reduced by one day ($t_{step}$=1) from 26 days and checked for fit of integral form of zero, first and second order equation. One such case is shown in FIGS. 10E, 10F and 10G, where integral form of zero, first and second order are checked for their fit for dataset of 10 days (t–16 days). The value of $R^2$ determined for integral form of zero, first and second order is found to be 0.90, 0.91 and 0.92 respectively. As seen from FIG. 10G, the value of $R^2$ determined to be less than the thresholds value of 0.95. Hence the dataset is further reduced by one step ($t_{step}$=1) from 10 days and checked for fit of integral form of zero, first and second order equation. One such case is shown in FIG. 10H, where integral form of zero order is checked for its fit for dataset of 5 days. The value of $R^2$ determined is 0.96, which is found to be greater than the thresholds value of 0.95.

Figure 10I:
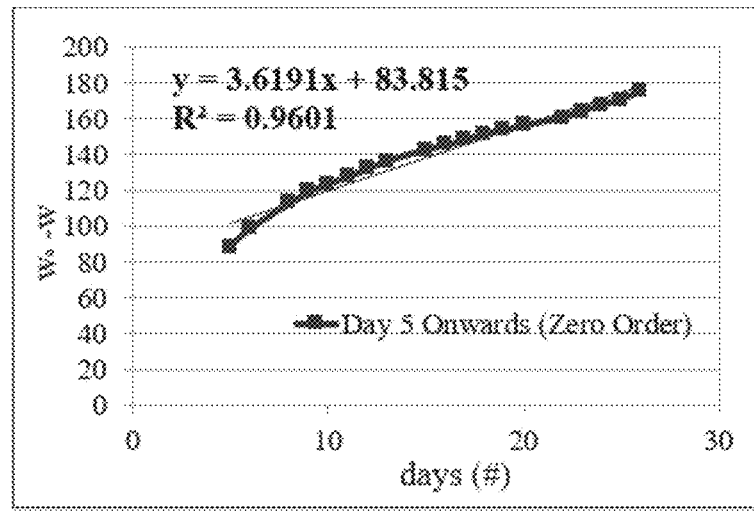
Figure 10J:
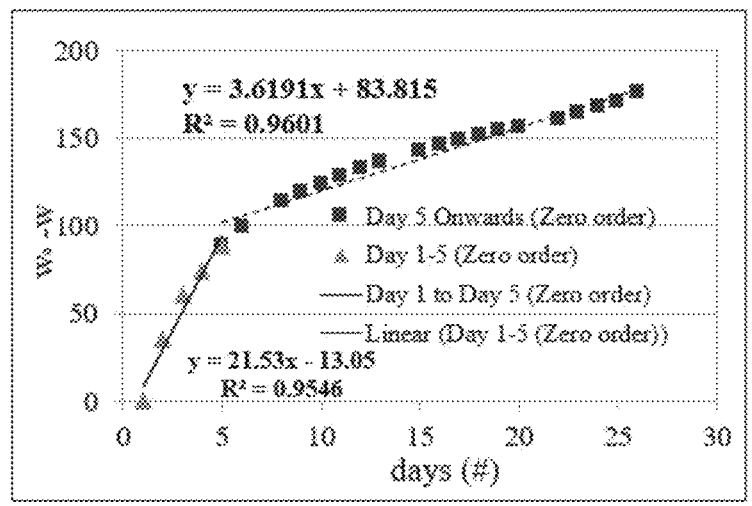

As seen from FIG. 10I, the value of $R^2$ is greater than the threshold value of $R^2$ and hence order of reaction is '0', zero order reaction. The data from t=0 to t=5 (t=n−1) is considered as the first stage; Further the data set is selected from t=n−1 (i.e. 5 days) to n (i.e. 26 days) and tried to fit the integral form of zero, first and second order as described earlier. The one such case is shown in FIG. 10J, where integral form of zero order is checked for its fit for dataset from 5 days to 26 days. The value of $R^2$ determined is 0.96, which is found to be greater than the thresholds value of 0.95. As seen from FIG. 10I, the value of $R^2$ is greater than the threshold value of R2 and hence order of reaction is –'0', zero order reaction for the data set from t=5 days to t=26 days. Hence the stage from time t=5 to t=26 days is considered as second stage.

The use of zero order rate kinetics with specific rate constant for data from t=0 days to t−5 days is considered as stage 1 and the use of zero order reaction rate kinetics for data from t=5 days to t=29 days is considered as stage 2. The multistage rate kinetic models (combined first stage and second stage) is shown in FIG. 10J.

Figure 10K:
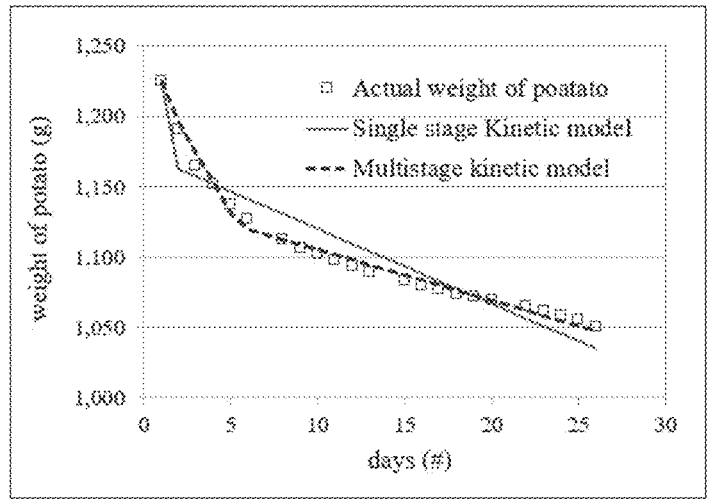
FIG. 10K illustrates a plot showing comparison of the multistage rate kinetics described with reference to FIGS. 10H-10J with single stage kinetics (illustrated with reference to FIG. 10A).

Herein, the multistage rate kinetics described with reference to FIGS. 10H-10J was compared with single stage kinetics (illustrated with reference to FIG. 10A). The result of comparison is illustrated in FIG. 10K. As is seen, the root mean square error (RMSE) for the Single stage rate kinetic model is determined to be 13.1 while the RMSE for the multi-stage rate kinetic model was determined to be 4.1.

In an embodiment, the root mean square error (RMSE) is computed by using the equation:

$$RMSE = \sqrt{\frac{\sum_{i=1}^{i=N}(Predicted_i - Actual_i)^2}{N}}$$

An example scenario describing shelf-life prediction of food items, and mathematical model therefor is described further with reference to FIGS. 11A-11K.

Example Scenario:

Referring now to FIGS. 11A-11K, in an example scenario, the shelf life study of food items has been carried out and mathematical models are developed to predict the shelf life of these food items. Example of the shelf life study performed with potato is shown in FIGS. 11A-11D. As seen in FIGS. 11A-11D, potatoes are stored at different environmental conditions to mimic the variations in temperature and humidity during different seasons, different geographies and different conditions in the storage house. The experiments were performed at 1) Temperature 23° C., Relative humidity (RH) 70% in presence of light 2) Temperature 20° C., RH 90% in absence of light (dark condition), 3) Temperature 25° C., RH 40% in presence of light 4) Temperature 10° C., RH 90% in absence of light (dark condition). It has been observed that the potatoes stored at 20° C. and 25° C. have shown very low shelf life as sprouting is observed after 3 to 7 days. The potatoes stored in absence of light (dark) conditions have shown white sprouts whereas potatoes stored in light have shown green sprouts. The green colour sprouts contain the toxic compound called solanine, which should be avoided for human consumption. The potatoes stored at lower temperature of 10° C. and higher relative humidity (90%) have shown no sprouting for the studied period and hence shown longer shelf life. The developed platform has provision to use the physics based, data based, rate kinetics based and Image based models to predict the shelf life of the food items. These models can predict the shelf life in terms of at least one of the shelf life defining parameter such as moisture loss, sprout formation, sugar content and the quality of the processed food prepared from the agricultural food item. For example, the quality of chips prepared from potatoes stored at different conditions.

Food items continuously lose moisture to the environment and hence lead to loss in weight. The weight loss affects both freshness of the food item and food loss as that much amount of food is not utilized for the desired use resulting into economic loss. Hence moisture loss is one of the important parameter that can be directly related with the degree of food freshness. Higher the moisture loss lower is the food freshness and so on. Table II in (FIG. 11E) shows the total weight loss from the potatoes stored at two different environmental conditions 1) Temperature 25° C., RH 40% in presence of light and 2) Temperature 10° C., RH 90% in absence of light (dark condition). As seen in Table II, the potatoes stored at low temperature of 10° C. and RH of 90% have shown low moisture loss compared to the moisture loss in potatoes stored at higher temperature of 25° C. and corresponding RH of 40%. Hence, the potatoes stored at environmental condition of 10° C. and RH of 90% has higher shelf life.

As disclosed herein, various attributes defining the shelf-life of food item may include, but are not limited to moisture, weight loss, composition (for example, sugar, starch, proteins, fats, vitamins), toxins, sprouting, color and/or flavor. In an experimental setup various factors affecting shelf-life of potato included, environmental factors such as temperature, humidity, lighting and ventilation; chemicals/preservative (for example, sprout preventing), initial conditions during harvesting (for example, moisture and/or texture after harvesting); cultivator (for example, Kufri or Atlanta). Various attributes considered for shelf-life prediction included moisture content, water activity, sugar, starch, protein content, and microorganisms (Cell count). Various sensory parameters included colour, mould and yeast formation, taste and smell. As described with reference to FIGS. 8, 9A and 9B, embodiments herein disclose Multistage multi-order rate kinetics for multiple attribute based shelf life estimation. Herein, $$\frac{d[A]}{dt} = k[A]^n$$

$$t_s = \frac{f([A_s])}{k}$$

Where, A represents food attribute, n reaction order, k rate constant, and $t_s$ shelf life of the food item.

Figure 11A:
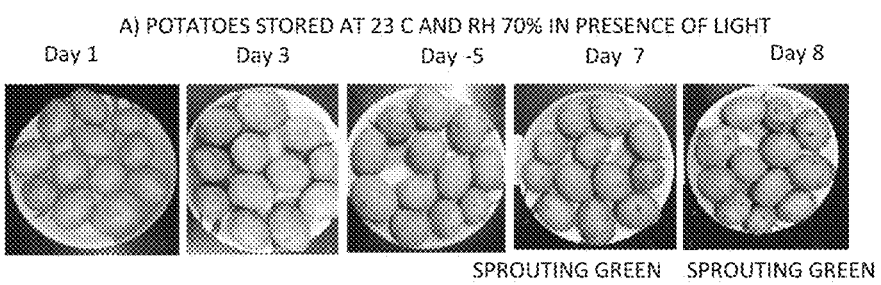
FIGS. 11A-11D illustrate potatoes stored at different environmental conditions, according to an example embodiment of the present disclosure.
Figure 11B:
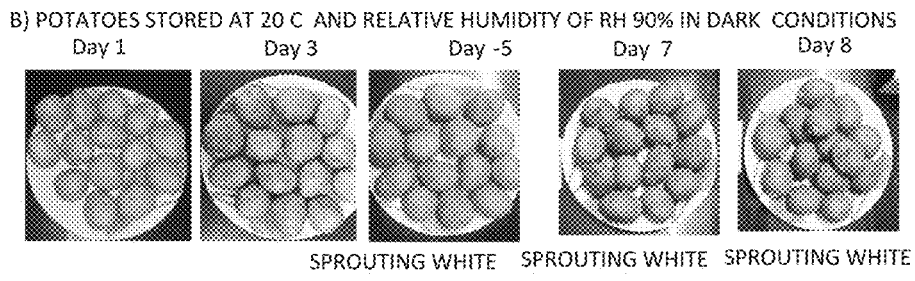
Figure 11C:
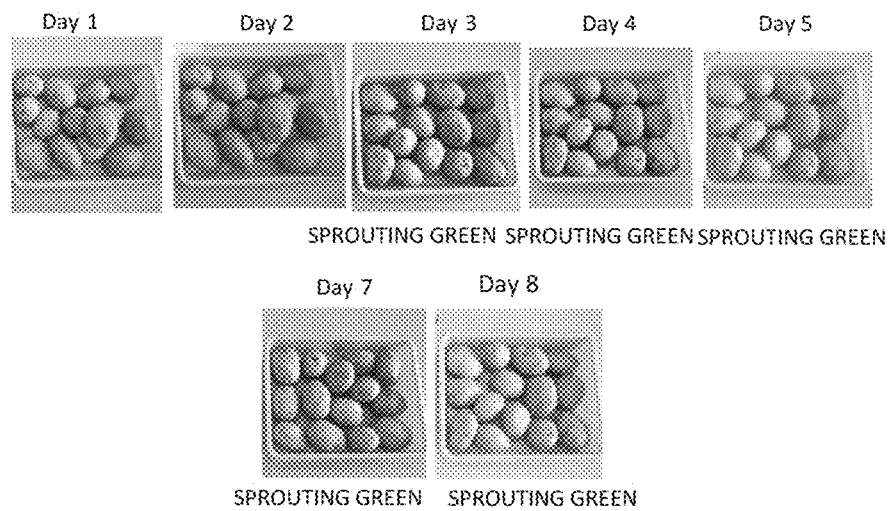
Figure 11D:
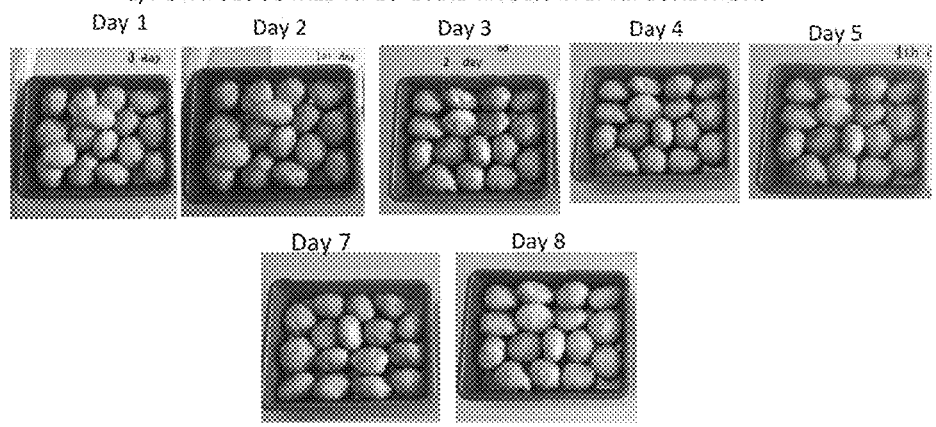
Figures 11E, 11F:
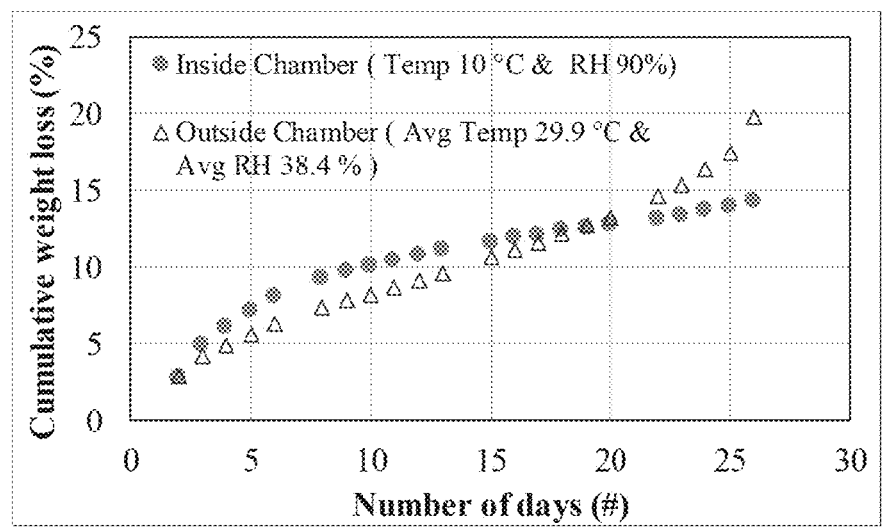
FIG. 11E illustrates a table (Table II) depicting total weight loss from the potatoes stored at two different environmental conditions, according to an example embodiment of the present disclosure.
FIG. 11F illustrates variation of cumulative weight loss of potatoes with number of days, according to an example embodiment of the present disclosure.

FIG. 11F illustrates variation of cumulative weight loss of potatoes with number of days, in accordance with the example scenario. As illustrated in FIG. 11F, in a weight loss study conducted for the potatoes, the potatoes inside the enclosure have shown higher weight loss initially but later stabilized.

Figure 11G:
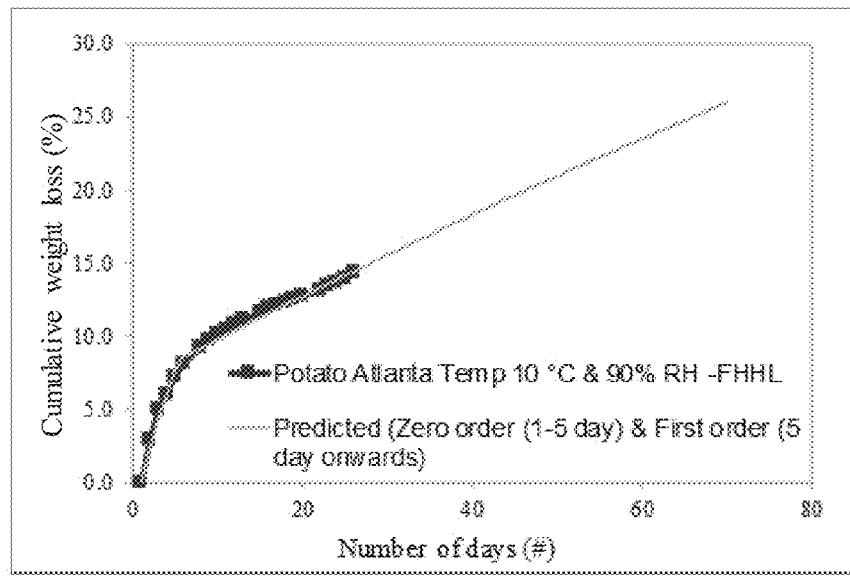
FIGS. 11G-11H illustrates experimental and predicted shelf life respectively based on the weight loss data, according to an example embodiment of the present disclosure.
Figure 11H:
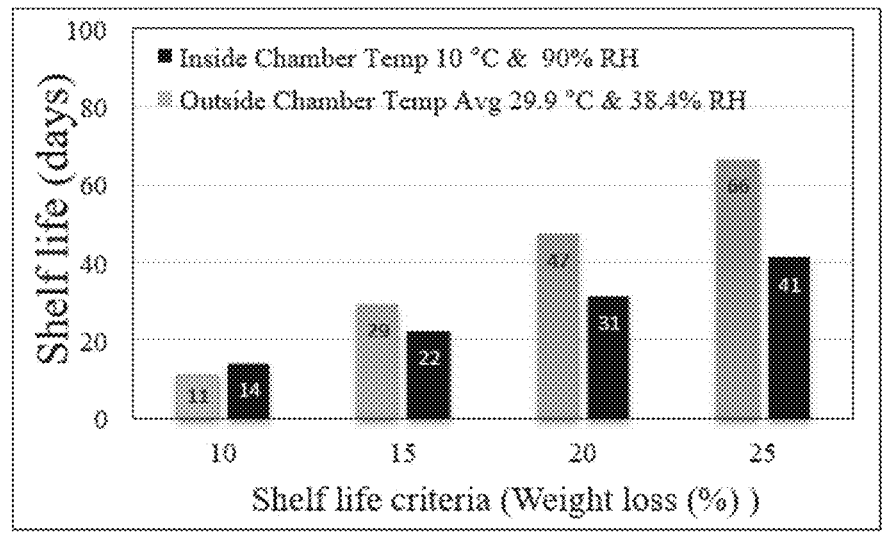

FIGS. 11G-11H illustrates experimental and predicted shelf life respectively based on the weight loss data, in accordance with the example scenario.

FIGS. 11I-11L illustrates rate kinetic models for potatoes stored at different environmental conditions, in accordance with the example scenario.

Figure 11M:
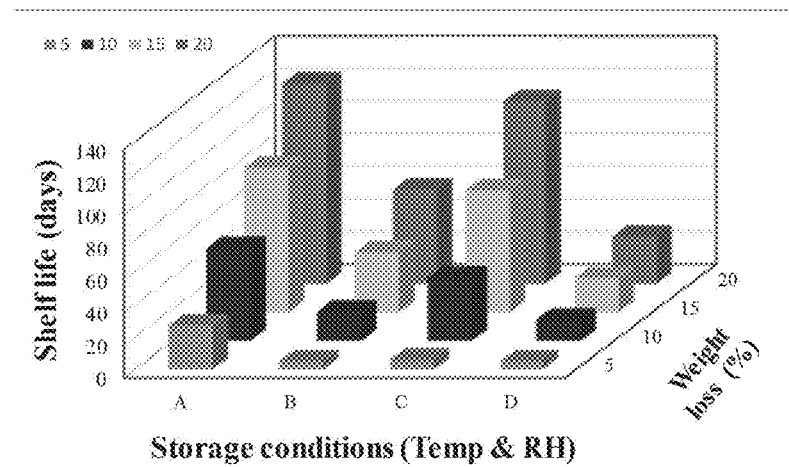
FIGS. 11M-11N illustrates shelf life prediction at different storage conditions on the basis of weight loss data, according to an example embodiment of the present disclosure.
Figure 11N:
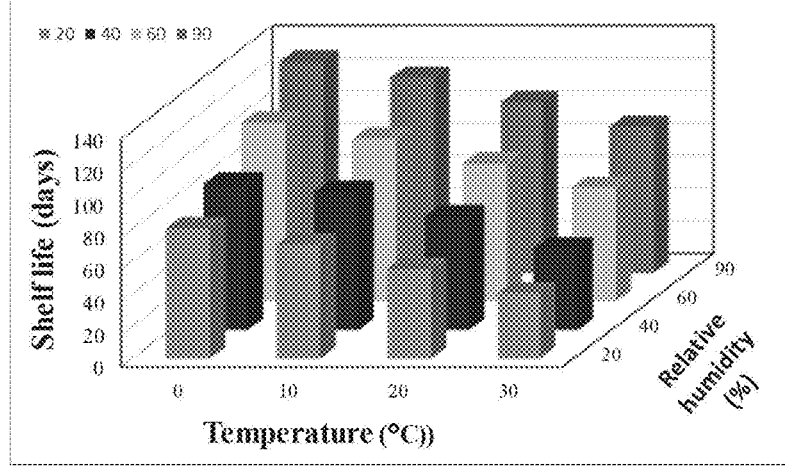

FIGS. 11M-11N illustrates shelf life prediction at different storage conditions on the basis of weight loss data, in accordance with the example scenario.

Figure 11O:
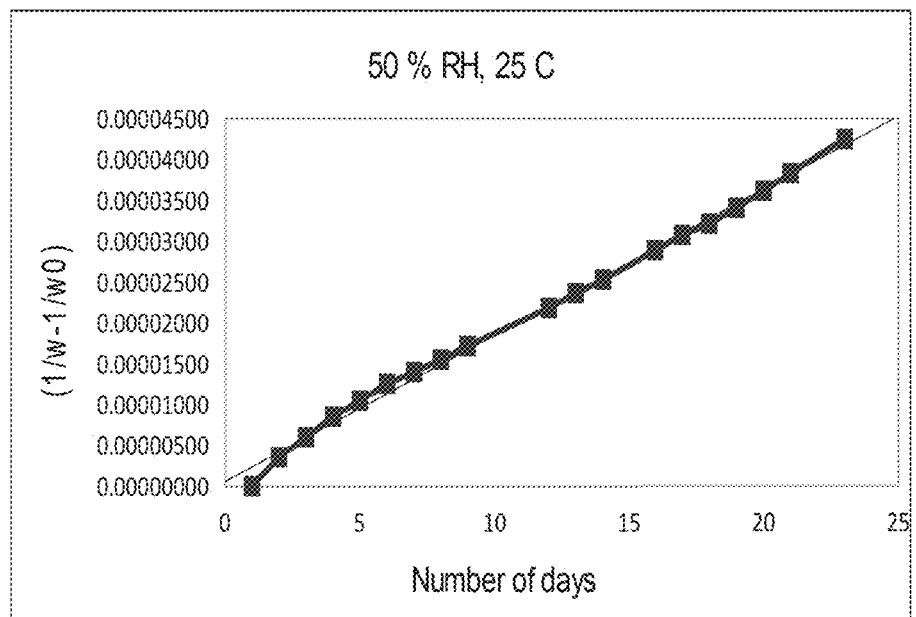
FIG. 11O-11P illustrates second order rate kinetics for Jyoti variety (cultivar) of potatoes, according to an example embodiment of the present disclosure.
Figure 11P:
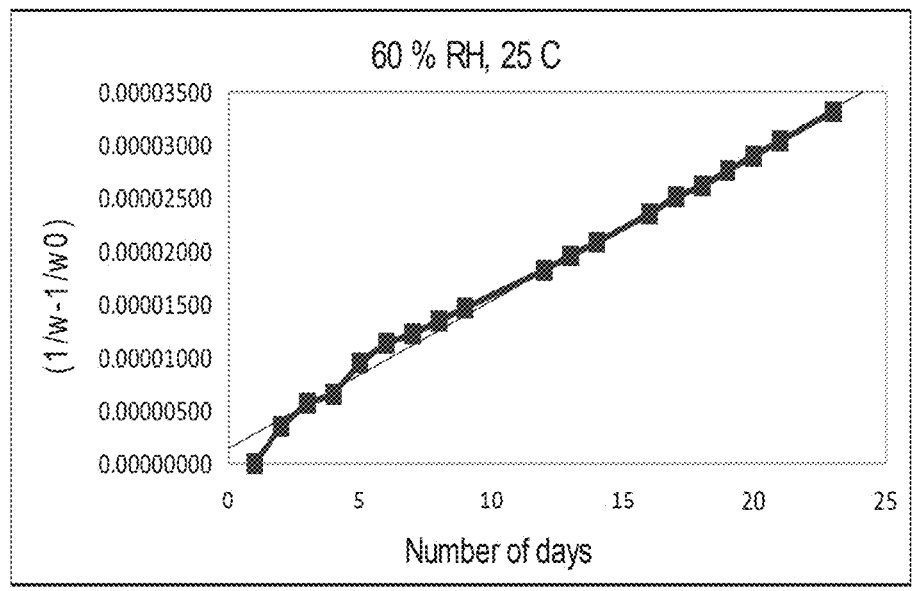

FIGS. 11O-11P illustrates second order rate kinetics for Jyoti variety (cultivar) of potatoes, in accordance with the example scenario. At same temperature but different humidity conditions.

Figures 11Q, 11R:
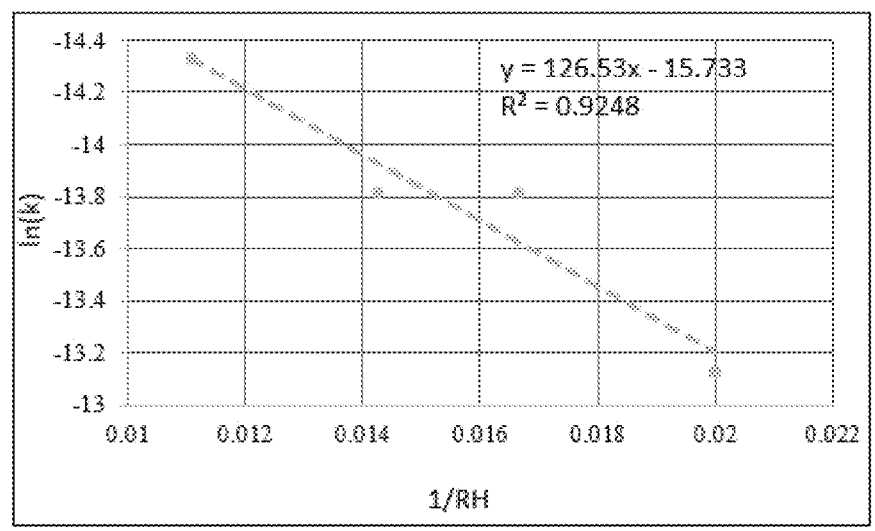
FIG. 11Q illustrates a tabular data applying Arrhenius type equation to capture humidity dependence on weight loss for a variety (Jyoti) of potatoes, in accordance with the example scenario.
FIG. 11R illustrates an example for estimating parameters of Arrhenius type equation at 25° C., in accordance with the example scenario.

FIG. 11Q illustrates a tabular data applying Arrhenius type equation to capture humidity dependence on weight loss for a variety (Jyoti) of potatoes, in accordance with the example scenario. In an embodiment, the Arrhenius-type equation for weight loss is:

$$W = \frac{W_o}{\left(1 + \left(W_o \times K_o \times d \times e^{\frac{m}{H}}\right)\right)}$$

Herein W is predicted weight, Wo is initial weight, Ko—pre-exponential factor, d—number of days, m is constant (specific to cultivars), and H is relative humidity.

In order to capture the effect of relative humidity, the rate kinetic models are developed for each of the plurality of post-harvest life cycle stages of the food. This model comprises one or more parameters calculated using Arrhenius type equation. The Arrhenius type equation has parameters comprising a pre-exponential factor (KO), cultivar (variety) specific constant (m). These parameters are calculated using the time-series data at a plurality of distinct relative humidity. The equation stands for constant temperature. FIG. 11R illustrates an example for estimating parameters of Arrhenius type equation at 25° C. Same approach can be useful for different temperatures.

FIG. 11S illustrates an example of shelf life attribute for various storage conditions, in accordance with the example scenario. This can be used as a lookup table for predicting shelf life depending upon the specific food attribute required for specific application. This can be also used for predicting the minimum shelf life comparing all the food attributes.

Various embodiments disclosed herein provides method and system for monitoring and quality evaluation of perishable food items. Said monitoring and quality evaluation facilitates in determining shelf-life (or remaining shelf-life of the food items). Freshness of perishable food items and/or shelf-life thereof is determined as a function of many multivariate, mutually exclusive varying parameters via a networked framework. The system enables developing continuous controlled monitoring technique by recreating the environmental conditions present at source, during transit or storage, in the custom enclosed chamber to predict freshness of perishable food items at source, during transit and storage. The disclosed framework may be able of controlling the environmental conditions in the enclosed chamber containing food item to maintain the favorable conditions surrounding the food items.

An important contribution of the disclosed embodiments is determination of freshness of the food item in quantitative terms. In an embodiment, the quantitative determination of freshness of the food items is based on receipt of sensor data as well as visual data pertaining to the food items. In an embodiment, inclusion of visual contents using CNNs fine-tuning (described with reference to FIGS. 6, 7A-7C) provides updated visual embedding of the food item, which is a vectorized representation of the food item that depicts visual freshness characteristics thereof. In an embodiment, the disclosed system can be used to develop Internet of Things (IoT) platform, in which the synchronized data output obtained at specified intervals can be interfaced with cloud/Personal Computer (PC). The quantified data can be displayed on a mobile screen, iPad, tablets and so on, through cloud/Wi-Fi module/gsm-module. In another embodiment, a rate kinetic based model (described with reference to FIGS. 8-11K) is utilized for determining reaction rate order of the food item at a particular post-harvest stage of the food item so as to determine the remaining shelf life thereof.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. A processor implemented method, comprising:
   obtaining input data comprising visual data and sensory data associated with a food item enclosed in a networked framework, via one or more hardware processors, wherein the visual data and sensory data are time-series data and comprises characteristics indicative of freshness of the food item at a plurality of lifecycle stages;
   obtaining, via the one or more hardware processors, a food freshness vector using the input data and one or more machine learning (ML) models, wherein obtaining the food freshness vector comprises:
      generating, by a pre-trained convolution neural network (CNN) model, a first vector embedding of the food item at a time-instance using the visual data, the pre-trained CNN model trained as a generic food item classifier using a plurality of images comprising the visual data of a plurality of food items for a plurality of time-instances associated with the plurality of lifecycle stages;
      concatenating the first vector embedding and a second vector embedding to obtain a concatenated vector embedding at the time-instance, wherein the second vector embedding obtained from the sensory data of the input data;
      obtaining, by fine-tuning the pre-trained CNN model along with the training of a Recurrent Neural Network (RNN), a third vector embedding associated with the food item at the time instance using the concatenated vector embedding, wherein the third vector embedding indicative of a lifecycle stage of the food item at the time instance, wherein the RNN is trained using the time series data of the visual data and the sensory data of the food item aging over a period of time, and comparing, using vector similarity measure, a food freshness vector of the food item at the lifecycle stage from amongst the plurality of lifecycle stages with a digital signature of the food item, via the one or more hardware processors, wherein the food freshness vector of the food item obtained by feeding the visual input of the food item to the fine-tuned CNN model, and wherein the digital signature of the food item is a digitized vector representation of the food item, indicative of freshness of the food item at a target lifecycle stage.

2. The method of claim 1, wherein during the training of the RNN model, the pre-trained CNN model is fine-tuned to obtain a fine-tuned CNN model, the fine-tuned CNN model being a weight shared model such that a plurality of weights associated with the pre-trained CNN model are updated by a plurality of gradients received from the plurality of time-instances of the RNN model.

3. The method of claim 2, wherein the digital signature of the food item is obtained by feeding visual input of the target food item to the fine-tuned CNN model.

4. The method of claim 1, wherein the sensory data comprises weight of the food item, weight loss of the food item, moisture content in the food item, moisture loss during the storage, concentration of specific compound in the food item, and concentration of specific gas such as Carbon dioxide ($CO_2$), ethylene ($C_2H_4$), ammonia ($NH_3$) released by the food item.

5. The method of claim 1, further comprises collecting the visual data and the sensory data using at least one of an invasive and a non-invasive technique, the invasive techniques comprises use of laboratory methods to calculate different food compositional parameters including at least one of sugar, starch, fat, protein, vitamins and antioxidants, and the non-invasive technique comprises at least one of a plurality of non-invasive sensors, the plurality of non-invasive sensors comprises gas sensors, acoustics, optical sensors, and near infrared sensor.

6. A system (300) comprising:
   one or more memories (304); and
   one or more hardware processors (302), the one or more memories (304) coupled to the one or more hardware processors (302), wherein the one or more hardware processors (302) are configured to execute programmed instructions stored in the one or more memories (304), to:
      obtain input data comprising visual data and sensory data associated with a food item enclosed in a networked framework, wherein the visual data and sensory data are time-series data and comprises characteristics indicative of freshness of the food item at a plurality of lifecycle stages;
   obtain a food freshness vector using the input data and one or more machine learning (ML) models, wherein obtaining the food freshness vector comprises:
      generate, by a pre-trained convolution neural network (CNN) model, a first vector embedding of the food item at a time-instance using the visual data, the pre-trained CNN model trained as a generic food item classifier using a plurality of images comprising the visual data of a plurality of food items for a plurality of time-instances associated with the plurality of lifecycle stages;
      concatenate the first vector embedding and a second vector embedding to obtain a concatenated vector embedding at the time-instance, wherein the second vector embedding obtained from the sensory data of the input data;
      obtain, by fine-tuning the pre-trained CNN model along with the training of a Recurrent Neural Network (RNN), a third vector embedding associated with the food item at the time instance using the concatenated vector embedding, wherein the third vector embedding indicative of a lifecycle stage of the food item at the time instance, wherein the RNN is trained using the time series data of the visual data and the sensory data of the food item aging over a period of time, and compare, using vector similarity measure, the food freshness vector of the food item at the lifecycle stage from amongst the plurality of lifecycle stages with a digital signature of the food item, wherein the food freshness vector of the food item obtained by feeding the visual input of the food item to the fine-tuned CNN model, and wherein the digital signature of the food item is a digitized vector representation of the food item, indicative of freshness of the food item at a target lifecycle stage.

7. The system of claim 6, wherein the one or more hardware processors are further configured by the instructions to fine-tune the pre-trained CNN model during the training of the RNN model, to obtain a fine-tuned CNN model, the fine-tuned CNN model being a weight shared model such that a plurality of weights associated with the pre-trained CNN model are updated by a plurality of gradients received from the plurality of time-instances of the RNN model.

8. The system of claim 7, wherein the one or more hardware processors are further configured by the instructions to obtain the digital signature of the food item by feeding visual input of the target food item to the fine-tuned CNN model.

9. The system of claim 6, wherein the sensory data comprises weight of the food item, weight loss of the food item, moisture content in the food item, moisture loss during the storage, concentration of specific compound in the food item, and concentration of specific gas such as Carbon dioxide ($CO_2$), ethylene ($C_2H_4$,), ammonia ($NH_3$) released by the food item.

10. The system of claim 6, wherein the one or more hardware processors are further configured by the instructions to collect the visual data and the sensory data using at least one of an invasive and a non-invasive technique, the invasive techniques comprises use of laboratory methods to calculate different food compositional parameters including at least one of sugar, starch, fat, protein, vitamins and antioxidants, and the non-invasive technique comprises at least one of a plurality of non-invasive sensors, the plurality of non-invasive sensors comprises gas sensors, acoustics, optical sensors, and nuclear magnetic sensor.

11. One or more non-transitory machine readable information storage mediums comprising one or more instructions which when executed by one or more hardware processors cause:

obtaining input data comprising visual data and sensory data associated with a food item enclosed in a networked framework, via one or more hardware processors, wherein the visual data and sensory data are time-series data and comprises characteristics indicative of freshness of the food item at a plurality of lifecycle stages;

obtaining, via the one or more hardware processors, a food freshness vector using the input data and one or more machine learning (ML) models, wherein obtaining the food freshness vector comprises:

generating, by a pre-trained convolution neural network (CNN) model, a first vector embedding of the food item at a time-instance using the visual data, the pre-trained CNN model trained as a generic food item classifier using a plurality of images comprising the visual data of a plurality of food items for a plurality of time-instances associated with the plurality of lifecycle stages;

concatenating the first vector embedding and a second vector embedding to obtain a concatenated vector embedding at the time-instance, wherein the second vector embedding obtained from the sensory data of the input data;

obtaining, by fine-tuning the pre-trained CNN model along with the training of a Recurrent Neural Network (RNN), a third vector embedding associated with the food item at the time instance using the concatenated vector embedding, wherein the third vector embedding indicative of a lifecycle stage of the food item at the time instance, wherein the RNN is trained using the time series data of the visual data and the sensory data of the food item aging over a period of time, and comparing, using vector similarity measure, a food freshness vector of the food item at the lifecycle stage from amongst the plurality of lifecycle stages with a digital signature of the food item, via the one or more hardware processors, wherein the food freshness vector of the food item obtained by feeding the visual input of the food item to the fine-tuned CNN model, and wherein the digital signature of the food item is a digitized vector representation of the food item, indicative of freshness of the food item at a target lifecycle stage.

* * * * *